(12) United States Patent
Lawson et al.

(10) Patent No.: US 11,013,910 B2
(45) Date of Patent: May 25, 2021

(54) DEVICES, METHODS, AND SYSTEMS FOR THE TREATMENT AND/OR MONITORING OF DAMAGED TISSUE

(71) Applicant: Adlore, Inc., Kalamazoo, MI (US)

(72) Inventors: Daryl Lawson, Kalamazoo, MI (US); Christopher Brian Arena, Blacksburg, VA (US)

(73) Assignee: Adlore, Inc., Kalamazoo, MI (US)

( * ) Notice: Subject to any disclaimer, the term of this patent is extended or adjusted under 35 U.S.C. 154(b) by 68 days.

(21) Appl. No.: 16/267,635

(22) Filed: Feb. 5, 2019

(65) Prior Publication Data
US 2019/0240475 A1 Aug. 8, 2019

Related U.S. Application Data

(60) Provisional application No. 62/627,028, filed on Feb. 6, 2018.

(51) Int. Cl.
*A61N 1/04* (2006.01)
*A61F 7/00* (2006.01)
(Continued)

(52) U.S. Cl.
CPC .............. *A61N 1/0468* (2013.01); *A61B 5/01* (2013.01); *A61B 5/0531* (2013.01);
(Continued)

(58) Field of Classification Search
CPC ................ A61N 1/0468; A61N 1/0484; A61N 1/36031; A61B 5/0531; A61B 5/01;
(Continued)

(56) References Cited

U.S. PATENT DOCUMENTS

| 5,974,342 A | 10/1999 | Petrofsky |
| 6,094,599 A * | 7/2000 | Bingham ............. A61N 1/0484 607/149 |

(Continued)

OTHER PUBLICATIONS

International Search Report for PCT/US2019/16596 dated Apr. 30, 2019; 2 pages.
(Continued)

*Primary Examiner* — Rex R Holmes
(74) *Attorney, Agent, or Firm* — Warner Norcross + Judd LLP

(57) ABSTRACT

Disclosed are methods, devices, and systems for treatment of an abnormal wound healing response. The methods, devices, and systems can be used to treat solid ulcerated tissue, such as diabetic foot ulcers (DFUs), arthritic tissue, muscle soreness, joint pain, varicose veins, obesity, and peripheral artery disease. Additionally, the methods, devices, and systems can promote the healing of xenograft, allograft, autograft, or engineered tissue following reconstruction surgery. The methods, devices, and systems include the ability to determine an optimal set of pulse parameters that are specific to wound healing. In embodiments, the methods, devices, and systems include components for guiding the user on electrode placement based on anatomical or electrical measurements, delivering a custom series of electric pulses, applying heat, and using feedback from physiologic measurements to control the device.

21 Claims, 10 Drawing Sheets

(51) Int. Cl.
*A61N 1/36* (2006.01)
*A61B 5/0531* (2021.01)
*A61B 5/01* (2006.01)
*A61B 5/145* (2006.01)
*A61F 7/02* (2006.01)
*A61F 7/03* (2006.01)

(52) U.S. Cl.
CPC ...... *A61B 5/14507* (2013.01); *A61B 5/14539* (2013.01); *A61F 7/007* (2013.01); *A61F 7/02* (2013.01); *A61N 1/0484* (2013.01); *A61N 1/36031* (2017.08); *A61F 7/032* (2013.01); *A61F 2007/0043* (2013.01); *A61F 2007/0045* (2013.01); *A61F 2007/0075* (2013.01); *A61F 2007/0078* (2013.01); *A61F 2007/0093* (2013.01)

(58) Field of Classification Search
CPC ... A61B 5/14507; A61B 5/14539; A61F 7/02; A61F 7/007; A61F 7/032; A61F 2007/0078; A61F 2007/0093; A61F 2007/0043; A61F 2007/0045; A61F 2007/0075
See application file for complete search history.

(56) References Cited

U.S. PATENT DOCUMENTS

| | | | |
|---|---|---|---|
| 7,144,390 | B1 | 12/2006 | Hannigan et al. |
| 7,483,738 | B2 | 1/2009 | Tamarkin et al. |
| 7,540,848 | B2 | 6/2009 | Hannigan et al. |
| 7,689,285 | B2 | 3/2010 | Garabet |
| 8,372,022 | B2 | 2/2013 | Hannigan et al. |
| 8,388,562 | B2 | 3/2013 | Baker et al. |
| 8,827,941 | B2 | 9/2014 | Davis et al. |
| 8,840,573 | B2 | 9/2014 | Neustaedter et al. |
| 8,882,687 | B2 | 11/2014 | Hannigan et al. |
| 9,333,282 | B2 | 5/2016 | Van Der Hulst |
| 9,526,816 | B2 | 12/2016 | Toth |
| D787,077 | S | 5/2017 | Lindsay |
| 9,642,414 | B2 | 5/2017 | Lindsay et al. |
| 9,724,243 | B2 | 8/2017 | Hannigan et al. |
| 10,058,478 | B2 | 8/2018 | Schnetz et al. |
| 10,130,805 | B2 | 11/2018 | Schonenberger et al. |
| 10,166,387 | B2 | 1/2019 | Bergelin et al. |
| 10,206,604 | B2 | 2/2019 | Bergelin et al. |
| 10,207,031 | B2 | 2/2019 | Toth |
| 2002/0026226 | A1* | 2/2002 | Ein ............... A61N 1/32 607/108 |
| 2004/0254624 | A1 | 12/2004 | Johnson |
| 2007/0016271 | A1* | 1/2007 | Hammond ....... A61F 7/007 607/96 |
| 2007/0264354 | A1 | 11/2007 | Herman |
| 2007/0282400 | A1 | 12/2007 | Gorham |
| 2008/0027509 | A1 | 1/2008 | Andino et al. |
| 2009/0240216 | A1 | 9/2009 | Hannigan et al. |
| 2010/0210983 | A1 | 8/2010 | Baker et al. |
| 2010/0268300 | A1 | 10/2010 | Ramos Leal et al. |
| 2010/0292746 | A1 | 11/2010 | Gorham |
| 2010/0318018 | A1 | 12/2010 | Schonenberger et al. |
| 2011/0125204 | A1 | 5/2011 | Louise |
| 2013/0158634 | A1 | 6/2013 | Ron Edoute et al. |
| 2013/0274629 | A1* | 10/2013 | Duesterhoft ....... A61B 5/0022 600/573 |
| 2013/0304007 | A1 | 11/2013 | Toth |
| 2013/0326912 | A1 | 12/2013 | Lindsay et al. |
| 2016/0015962 | A1 | 1/2016 | Shokoueinejad Maragheh et al. |
| 2016/0045735 | A1 | 2/2016 | Chang et al. |
| 2016/0081580 | A1 | 3/2016 | Bergelin et al. |
| 2016/0143555 | A1 | 5/2016 | Decre et al. |
| 2016/0184575 | A1 | 6/2016 | Schonenberger et al. |
| 2016/0213521 | A1 | 7/2016 | Bacon et al. |
| 2016/0213552 | A1 | 7/2016 | Lindsay |
| 2017/0296805 | A1 | 10/2017 | Mower |
| 2019/0388667 | A1* | 12/2019 | Xu ................ A61N 1/0428 |

OTHER PUBLICATIONS

Written Opinion of the International Searching Authority for PCT/US2019/16596 dated Apr. 30, 2019; 5 pages.

* cited by examiner

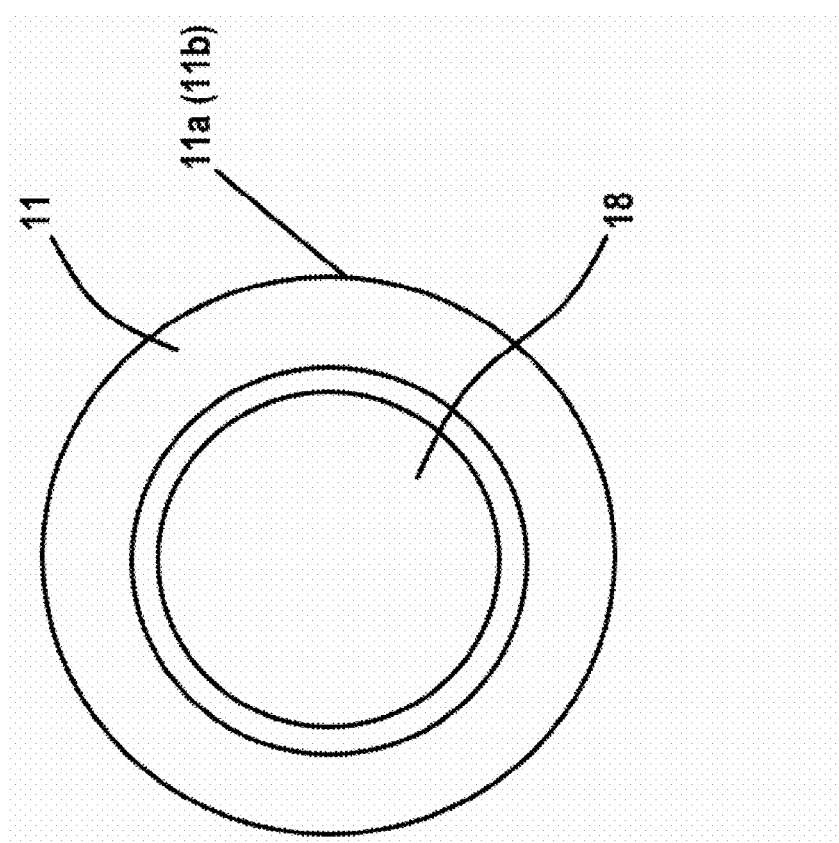

DEVICES, METHODS, AND SYSTEMS FOR THE TREATMENT AND/OR MONITORING OF DAMAGED TISSUE

This application claims the benefit of US Provisional application entitled DEVICE, METHODS, AND SYSTEM FOR THE TREATMENT OF WOUNDS, Ser. No. 62/627,028, filed on Feb. 6, 2018, which is incorporated by reference it its entirety herein.

FIELD OF THE INVENTION

This disclosure relates to devices, methods, and systems for the treatment of wounds.

BACKGROUND OF THE INVENTION

Diabetic foot ulcers (DFUs) are the cause of over 80,000 amputations each year in the United States. The number of people who lose a limb due to diabetes is expected to triple by the year 2050. Nationally, of the over $100 billion spent annually on managing diabetes, at least 33% is linked to the treatment of DFUs.

Often, poor-healing, neuropathic wounds that occur on diabetic patients, especially on the lower extremities, will only worsen if left untreated, in part due to impairment of blood flow. Patients who have diabetes experience reduced blood flow in the limbs, and ulcers often develop on the bottom of the foot.

There is, therefore, a need for treatment and/or monitoring of DFUs in a cost-effective manner that can prevent amputation.

SUMMARY OF THE INVENTION

Embodiments of the disclosure comprise devices, methods, and systems for the treatment and/or monitoring of damaged tissue, such as wounds. The devices, methods, and systems may be embodied in a variety of ways, and may provide the ability for electrical stimulation and heat treatment in at-home setting.

Accordingly, a therapeutic device is disclosed for treating damaged tissue. The device may include a heating component, which is configured to apply heat to a limb, and a plurality of electrodes, with at least one electrode configured to supply electrical stimulation, also to the limb.

In one aspect, the device may further include a plurality of sensors. Optionally, at least one sensor is configured to measure at least one indicator of wound healing.

In other embodiments, the device may also comprise a pulse generator being electrically coupled with the plurality of electrodes, wherein the pulse generator is configured to generate a plurality of electrical impulses for delivering electrical stimulation treatment to subject through at least one electrode.

The device may also comprise at least one control unit to operate the electrical pulse stimulation and the heating component. The device may, in certain embodiments, further comprise a processor, wherein the processor comprises processing logic and telemetry to determine a treatment regimen for increasing blood flow based on carry-over effects.

In another embodiment, the device may include one or more sensors to sense one or more physiological conditions of a person undergoing treatment. For example, the sensors may sense at least one indicator of wound healing.

Optionally, the method may include generating electrical pulses and applying the electrical pulses to the limb to generate electrical stimulation.

In other aspects, the method includes processing logic and telemetry to determine a treatment regimen for increasing, optionally maximizing, a wearer's blood flow based on carry-over effects.

In yet other aspects, the method includes collecting, and optionally recording, stimulation data and indicators of wound healing during treatment and after treatment.

In any of the above, suitable indicators may include physiologic, such as bioimpedance, pH, heat in the wound and lower extremity, periwound status measurements.

The method may further include enabling, disabling, and/or altering the electrical stimulation and/or heat based on the indicators. The method may additionally include determining future treatment parameters based on the indicators.

In yet another aspect, a system is disclosed that includes a processing device; and a non-transitory computer-readable medium communicatively coupled to the processing device, wherein the processing device is configured to perform operations comprising: receiving a data set associated with patient indicators of wound healing and stimulation data; storing the data set; generating treatment parameters based on the stored data set by determining a relationship between initial treatment parameters and plurality of the indicators of wound healing and the stimulation data; and electronically converting the stored data set into the next parameters based on the relationship. In certain embodiments, the system may further include a component for generating an interface for display that includes at least some of the data of the data set, which is associated with the indicators of wound healing and the stimulation data.

In another aspect, a method of treating damaged tissue is disclosed. The method may comprise the steps of applying heat and electrical simulation to or adjacent the damaged tissue.

In one aspect, the method includes applying heat and electrical simulation to at least a portion of the limb with the damaged tissue. Further, applying the heat includes applying the heat to at least 40%, or at least 50%, or at least 60%, or at least 70%, or at least 80%, or at least 90%, or about 100% of the portion of the limb to effect global warming of the limb.

In a further aspect, the method applying heat and electrical simulation to the limb with the damaged tissue. Further, applying the heat includes applying the heat to at least 40%, or at least 50%, or at least 60%, or at least 70%, or at least 80%, or at least 90%, or about 100% of the limb to effect global warming of the limb.

In one embodiment, the method applying heat and electrical simulation to the limb includes applying the heat to at least 40% of the limb.

In another aspect, the method includes identifying tissue to be treated; and placing a therapeutic device with a heating component and a plurality of electrodes on the limb, wherein the device surrounds and/or covers a significant portion of the limb; and applying heat to the limb and while simultaneously conducting an electrical current through the plurality of electrodes to apply electrical stimulation to the limb.

The method may further include selecting a treatment protocol.

In some embodiments, the method may include covering at least 90%, or at least 80%, or at least 70%, or at least 60%, or at least 50%, or at least 40%, or at least 20% of the limb.

In some embodiments, the method further includes sensing one or more physiological conditions of a person undergoing treatment. For example, the sensing may include sensing at least one indicator of wound healing. Additionally, the method may further include measuring the physiological condition, such as the indicator of wound healing.

Optionally, the method may include generating electrical pulses and applying the electrical pulses to the limb to generate electrical pulse.

In other aspects, the method includes processing logic and telemetry to determine a treatment regimen for increasing, optionally maximizing, wearers blood flow based on carry-over effects.

In yet other aspects, the method includes collecting, and optionally recording, stimulation data and indicators of wound healing during treatment and after treatment.

In any of the above, suitable indicators may include physiological and bioimpedance measurements.

The method may further include enabling, disabling, and/or altering the electrical stimulation and/or heat based on the indicators. The method may additionally include determining future treatment parameters based on the indicators.

In yet another aspect, a system is disclosed that includes a processing device; and a non-transitory computer-readable medium communicatively coupled to the processing device, wherein the processing device is configured to perform operations comprising: receiving a data set associated with patient indicators of wound healing and stimulation data; storing the data set; generating treatment parameters based on the stored data set by determining a relationship between initial treatment parameters and plurality of the indicators of wound healing and the stimulation data; and electronically converting the stored data set into the next parameters based on the relationship. In certain embodiments, the system may further include a component for generating an interface for display that includes at least some of the data of the data set, which is associated with the indicators of wound healing and the stimulation data.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE FIGURES

FIG. 1B is a schematic drawing of an electrode with a sensor integrated or co-located with the electrode;

DETAILED DESCRIPTION

As will be more fully described below, disclosed herein are devices, methods, and systems for treating and/or monitoring damaged tissue, including treating and/or monitoring ulcers, such as diabetic ulcers. The disclosed devices, methods, and systems may reduce the risk of wound infection, treat infection, and/or promote healing of damaged tissue, such as wounds, via the joint application of heat and electrical stimulation. The devices, methods, and systems may be embodied in a variety of ways. Further, although described in reference to a human or person, it should be understood that the devices, methods, and systems disclosed herein may also be used on animals.

Figure 1:
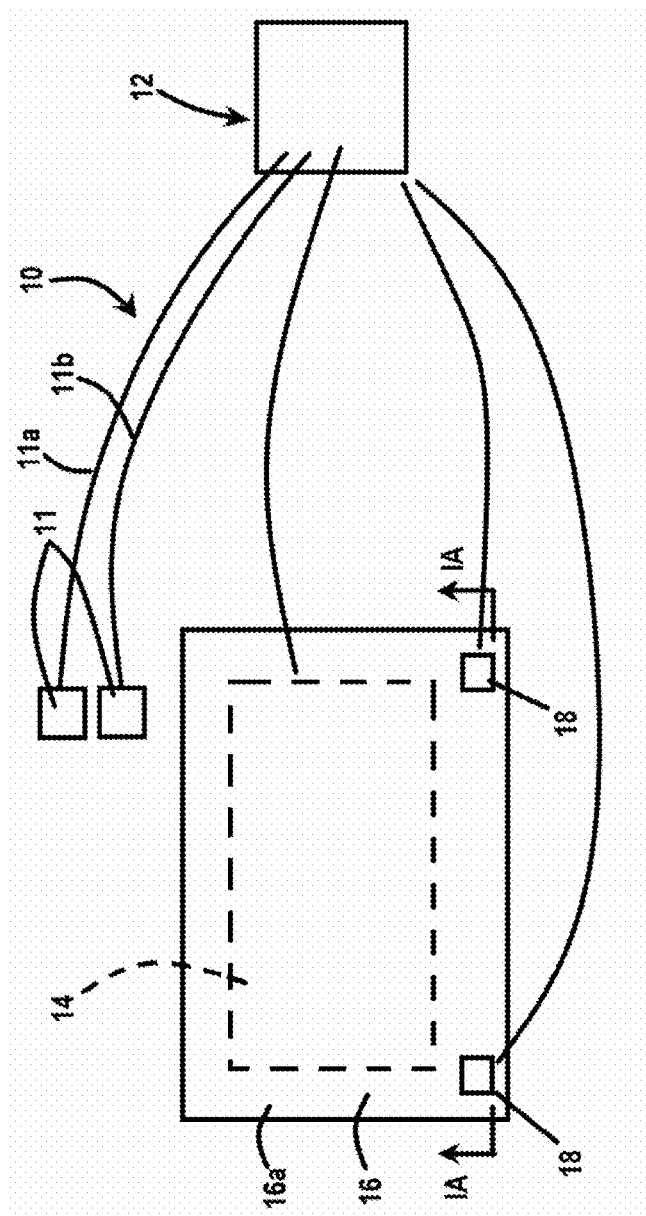
FIG. 1 is a schematic diagram illustrating one embodiment of a device for healing and/or monitoring damaged tissue.

Referring to FIG. 1, the numeral 10 generally designates a device for treating and/or monitoring damaged tissue, such as a wound. Device 10 includes at least two or more electrodes 11 for attaching to a person's limb at or near the damaged skin to apply electrical stimulation to the underlying tissue, including muscles, nerves, and optionally tendons. For example, electrodes 11 may include self-adhesive electrodes, including self-adhesive rubber electrodes, or taped-on electrodes. Optionally, the electrodes may comprises dry fabric electrodes from conductive thread or carbon electrodes for MRI compatibility.

Alternately, the electrodes 11 may be applied to a location remote from the damaged skin, for example, over a muscle or nerve that extends into the limb. See below discussion of additional embodiments for further discussions of suitable locations for the electrodes.

Device 10 also includes a control unit 12, which is powered by a battery or other source of current/voltage (such as a standard 120-volts wall outlet) and is in electrical communication with electrodes 11 via electrical leads 11a, 11b (FIG. 1) and configured to supply electrical current to at least one of the electrodes. Accordingly, depending on the type of current (AC/DC) and/or voltage provided or delivered to control unit 12, control unit 12 may include a converter (AC to DC or DC to AC) and a transformer to adjust (such as reduce or increase where applicable) the supplied voltage and one or more resistors to adjust (e.g. reduce) the current to suitable levels, described more fully below.

Optionally, control unit 12 includes a controller and a pulse generator, which is electrically coupled to the controller and to the source of electricity (either directly or through the controller via electrical leads), which can generate a plurality of electrical impulses for delivering an electrical pulse wave form to the at least one electrode for applying to the person's skin or tissue, to thereby administer the electrical pulse stimulation treatment through electrodes 11. Depending on where and how much current is applied, and where the electrodes are placed, the electrical stimulation may induce neuromuscular stimulation (NMES) or transcutaneous stimulation (TENS) or microtens (MCT) stimulation. Optionally, the pulse generator generates a biphasic pulse wave form, for example, a symmetric biphasic wave form. Again, for further discussion of suitable wave forms, reference is made to the description that follows.

Control unit 12 may be constructed of an electrical component, or group of electrical components, which are capable of carrying out the functions described herein. As noted, control unit 12 may include a controller, such as a conventional microcontroller or group of conventional microcontrollers. In general, the controller includes any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. When implemented to communicate with a remote device, including a server, a phone, a pad, or other hand held electronic device, the control unit 12 may include a communication device, such as a Bluetooth device, a WiFi device, or a micro USB, which can provide a communication interface with the remote device.

Where device 10 is configured for use in a home setting, the pulse generator may generate a biphasic pulse wave form with an amplitude in a range of 1-50 mA (milliamperes), or 10-40 mA, or 15-35 mA, and optionally about 20 mA depending on the desired stimulation. The pulse width may be in a range of 10-1000 μs (micro seconds), 50-800 μs, 300-500 μs, again depending on the desired stimulation. For example, for smaller muscles, a suitable amplitude may be around 30 mA and a pulse width may fall in a range of 50-200 μs. For example, for larger muscles, a suitable amplitude may be around 50 mA and a suitable pulse width may fall in a range of 300-500 μs. For nerves, a suitable amplitude may be around 20 mA and a suitable pulse width may fall in a range of 20-100 μs. It should be understood that these are exemplary only, and that the amplitude in milliamps and pulse width varies not only on the type of tissue but the habitus of the tissue being stimulated. The principles fall under the concept of the strength-duration curve. As a result, the amplitude of the current can vary based on the person and/or type of tissue to be stimulated and/or the type of tissue damage that is being treated and/or location of treatment. Further, as noted, the electrical current may be an AC current or DC current, and in some settings a high volt direct current (HVDC).

When configured for use in a medically supervised setting, these values may be adjusted. For example, in medically supervised setting, the pulse generator may generate a biphasic pulse wave form with an amplitude in a range of 0.25 mA to 100 mA, 10 mA to 75 mA, or optionally about 20 mA depending on the desired stimulation. The pulse width may be in a range of 50 to 500 μs, 100 to 300 μs, or optionally about 250 μs, again depending on the desired stimulation. For example, for smaller muscles, a suitable amplitude may be around 20 mA and a pulse width may be around 250 μs. For larger muscles, a suitable amplitude may be around 30 mA and a suitable pulse width may be about 300 μs. For nerves, a suitable amplitude may be around 20 mA and a suitable pulse width may fall in a range of 20-100 μs.

Optionally, in addition to electrical stimulation, electrodes 11 may be used to warm the tissue and, therefore, form a heating component. In order to achieve a warming effect, the pulse generator may generates a pulsed radio-frequency range in the range of 50-500 kHz, with an amplitude in the range of 1 to 100 V or 50 to 100V, and a duty cycle 1% to 100% (pulsed-to-continuous on-time). This could help to heat deep into the limb, especially if you place the electrodes on opposite sides. Further, the pulse generator may be adjustable and configured (e.g. by control unit 12) to switch between an electrical stimulation modality and a warming modality where different wave forms are desired for each desired effect.

Optionally, in lieu of or in addition to warming using electrodes 11, device 10 may include a separate heating component 14, which may be controlled by control unit 12. Heating component 14 may be in the form of an electric heating coil, an electronic heater, such as a Peltier device or infrared LEDS, or heated fluid (such as water that flows though channels or tubing), or chemical warmers that when bent or pressed start a chemical exothermic reaction. The heating component 14 is further configured so that it "globally" heats the limb (or portion of the limb) that includes the damaged tissue. The term "global" or "globally" refers to raising the temperature of the limb (or portion of the limb) and not just local warming of the limb where the limb surface and the tissue beneath the surface are warmed. To achieve global warming, heat is applied about 40%-100% of the limb or body part (or portion of the limb or body part), and optionally to at least at least 40%, or at least 50%, or at least 60%, or at least 80%, or at least 90%, or about 100%.

In one embodiment, globally warming the limb is achieved by wrapping the heating component 14 around the limb (or portion of the limb) so that it covers at least 20%, or at least 30%, or at least 40%, or at least 50%, or at least 60%, or at least 70%, or at least 80%, or at least 90%, or about 100% of the limb or body part (or portion of the limb or body part). To that end, heating component 14 may be mounted (including encasing it) in a covering 16 that is suitable for wrapping around the limb being treated. The covering may be in the form of a large patch of material or materials, including fabric, which may be assembled from multiples layers (e.g. 16a, 16b, and 16c), with the separate heating component sandwiched between two of the layers, and the layer 16a touching the person's skin being formed from a material that is comfortable to the touch. Optionally, two or more layers may be joined together to form a bladder for inflating the covering or for forming a conduit(s) through which warming fluid may be circulated to form the heating component.

Additionally, as described below, the patch may include a layer of thermally conductive material, for example, to transfer the heat to a greater area than the footprint of the heating component and/or a layer of thermally reflective material, either or both of which may increase the efficiency of the heat transfer from the heating component to the limb or body part. Optionally, electrodes 11 may be integrated into or simply be co-located with the covering 16 (e.g. placed under covering 16 on skin, but not necessarily attached to the covering).

To provide an efficient transfer of heat from the heating component 14 to the person's skin, heating component 14 is located adjacent layer 16a, which is placed on the person's skin. Optionally, as noted, to increase the efficiency, one or more of the layers (e.g. layer 16b) may form a thermally conductive and/or reflective layer to form an insulation layer, and may be formed from a heat reflective material, such as heat reflective thin plastic (such as a foil or a thin plastic sheet coated with a metallic reflecting agent, such as metallized polyethylene (MPET)). To protect the various layers and/or provide cushioning, layer 16c may comprise a protective outer layer, such as a foam, including neoprene. Alternately or in addition, as noted above and described below, one of the layers may be a thermally conductive layer to transfer the heat from the heating component across the limb—either to provide a more uniform distribution of the heat and/or to facilitate transfer of the heat beyond the immediate "footprint" of the heating component.

Additionally, the patch of fabric may be shaped to conform to the person's limb. For example, as described in reference to the embodiments described below, the covering or patch may be configured into the shape of a boot, covering the lower portion of a leg. For example, the covering may start at the knee and extend to and optionally enclose the foot, for example, in the case of treating ulcers on the heel of a person. Or the patch may be configured as a sleeve to cover an arm and/or shoulder, or other body part. For additional or alternate details of the various layers of material that can be assembled to form covering 16 and to encase the heating component, reference is made to FIG. 3 and the corresponding description.

Figure 1A:
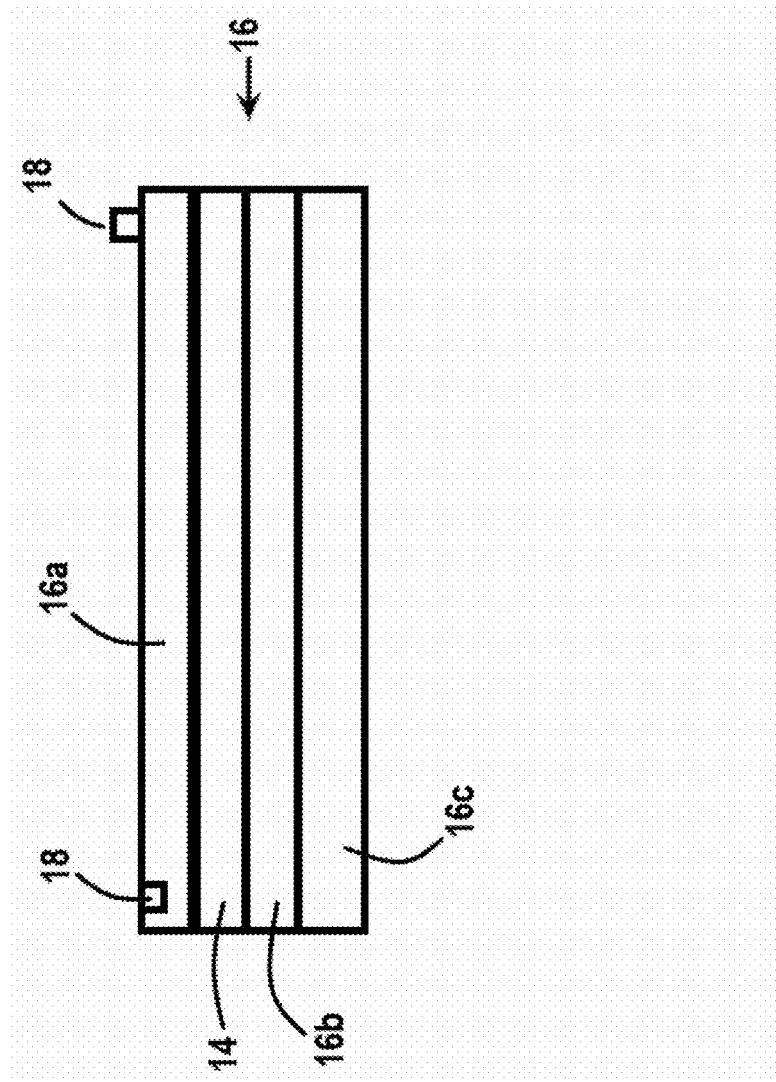
FIG. 1A is cross-section taken along line IA-IA of FIG. 1.

In another embodiment, described more fully in reference to the additional embodiments below, device 10 may include one or more sensors 18 in communication (electrical or wireless) with control unit 12. Similar to electrodes 11, sensors 18 may be separately mounted from the covering 16, co-located with covering 16, or integrated with covering 16. For example, similar to electrodes 11, sensors 18 may be located at the surface of layer 16a, for example, by surface mounting or flush mounting them to or in layer 16a (FIG. 1A). When separately mounted or co-located with covering 16, sensors 18 may be mounted to the skin of the person using an adhesive strip or an adhesive, including an adhesive with a very low pull force required for removable, such as a conductive adhesive gel, including HYDROGEL, which is tacky enough to hold a small device, such as a sensor, in place, especially when then covered by covering 16, but is easily removed to avoid damage to the person's skin.

Further, the sensor or sensors 18 may be co-located with and/or integrated with the electrode. For example, referring to FIG. 1B, the electrodes 11 may have an annular or donut shape with central opening (or a non-circular shape with an opening). The sensor, such as an optical sensor, including a blood flow sensor (e.g., IR LED+photodiode), can then be optionally co-located in the central opening of the electrode so that, for example, the electrode may hold the sensor in place. Further, it may be integrated into the electrode by commonly mounting the sensor with the electrode on a shared substrate on which both the sensor and electrode are mounted.

The sensors may be used to sense and, optionally, measure one or more physiological conditions of a person undergoing treatment and forward sensor signals to the microprocessor of the control unit 12, containing measurement data, for processing. In some embodiments, the data from the sensor signals may be sent to a remote location, for example, for monitoring the wound, which is more fully described below.

For example, the sensing may include sensing at least one condition that is an indicator of healing, such as wound healing, or the status of the damaged tissue, such as the wound, including whether there is an infection present. In one embodiment, sensors 18 may monitor stimulation data and indicators of wound healing during treatment and/or after treatment. Such indicators may be physiological, such as bioimpedance measurements, blood flow, blood flow volume, pH of the wound, temperature of the wound, temperature of the limb, sensor of periwound region for abnormal moisture or exudate. For example, control unit 12 may be configured to adjust the applied heat based on the sensor readings from the temperature sensor(s) and optionally provide closed loop feedback control of the heating component to avoid over heating or to increase the heat when the temperature is too low.

Suitable blood flow/blood volume sensors include photoplethysmography (PPG)-blood flow sensors and pulse oximeter sensors, which use two frequencies of light (red and infrared) to determine the percentage (%) of hemoglobin in the blood that is saturated with oxygen. The percentage is called blood oxygen saturation, or SpO2, which can be used to compute blood volume.

Suitable infections sensors include sensors to detect pH, including the use of in wound-pH strips, which change color in response to the pH levels; electro-chemical bio sensors; temperature sensors to detect wound temperature, including the use of in-wound temperature strips; or sensors that detect myeloperoxidase, including myeloperoxidase responsive materials; which change color in response to elevated myeloperoxidase levels. In any of the above noted visual indicators, electrical sensors (e.g., optical sensors) may then be used to detect the visual changes in the indicators, which can then be transmitted to the control unit 12.

Suitable sensors, as noted, include optical sensors (e.g. light sources combined with photodiodes to measure reflectance or absorption of the light in the tissue, for example to measure oxygen) and Doppler probes to measure blood flow; blood flow volume (BVP) sensor or photoplethysmography to measure blood flow volume; Hall Effect sensors or probes to monitor the stimulation current delivered to the skin; temperature sensors, such as skin temperature probes, to measure temperature; pH sensors; moisture sensors; or a voltage sensor, such as a differential high voltage probe, to measure the applied voltage to the skin or tissue.

To detect infection, sensors 18 may comprise: a pH sensor (e.g. measures activity of hydrogen ions in the tissue or blood) to measure the pH of the skin, with a low pH correlating to an oncoming infection; a temperature sensor to measure the temperature of the skin (as noted above), with an increase in heat being used to indicate an infection; and/or a moisture sensor, with an increase in moisture correlating to an infection. The sensor may detect moisture balance in and around the wound to help prevent maceration of the periwound area. A suitable moisture sensor includes an electrochemical bio sensor.

Accordingly, when an infection is detected or suspected, control unit 12 may be configured to stop operation of device 10 and, further, optionally generate a signal either locally (e.g. an alarm signal that generates a visual or audible notification) or remotely via a communication device (described above and below) to notify a third party, such as a nurse or doctor of the apparent infection.

In one embodiment, device 10 may switch between a treatment mode and a monitoring mode or device 10 may operate the modes together. For example, the monitoring mode may operate during pauses or temporal spaces between the pulsing of the electrical stimulation (so as not to interfere with the measurement) or between treatment phases. In one embodiment, control unit 12 may have a filter so that the two modes can operate simultaneously, to filter out the signals generated by the treatment when reading and processing the monitoring signals.

In any of the embodiments, device 10 may include a pressure sensor to detect the pressure and/or any shear applied to the wound. For example, control unit 12 may be configured to adjust treatment (e.g. reduce or stop the applied heat and/or inflation of the covering in the case of an inflatable covering) to off load pressure from the wound based on the readings of the pressure sensor to avoid constricting the body part, such as the foot or leg.

In any of the embodiments, device 10 may include a user input device, such as a switch or a button, for example on a touch screen, to allow a caregiver (either locally or remotely) or the user to turn off the therapy functions and allow the device to simple monitor the damage tissue, as noted above. The user input device may alternately or in addition allow a caregiver, as noted above, to select between therapy protocols or adjust the therapy protocols.

In another embodiment of device, device 10 may be configured as a monitoring device only, thereby eliminating the need for a heating component and/or electrodes.

Control unit 12 then may be configured to control the pulse generator (or current delivered to the pulse generator) to control the delivery of electrical stimulation provided by electrodes based on the sensor signals. As noted above, it may be configured to stop the treatment or may adjust the treatment based on input from a caregiver and/or based the sensor readings. To that end, the controller of control unit 12 optionally includes processing logic to determine a treatment regimen for increasing, optionally optimizing, such as by maximizing, the wearer's blood flow. For example, control unit 12 may stop or adjust one or more characteristics of the electrical stimulation, such as the wave form, including amplitude, duration, and pulse width based on input (sensor signals or user input). In this manner, control unit 12 can provide a closed loop feedback control of the treatment and/or monitoring of device 10.

In yet other aspects, control unit 12 may collect, and optionally record, stimulation data and indicators of wound healing during treatment and after treatment, which can be available for upload or download from control unit or, as noted above, transmitted to a remote location.

In another embodiment, control unit 12 may simply have a preset mode or program for operating the electrodes 11 and/or heating element 14. For example, control unit 12 may simply turn on the treatment device (based on input from a caregiver or user) and power the electrodes 11 and/or heating component for a preselected time period with a preselected electrical stimulation wave form and/or temperature, and hence include a timer. Alternately, control unit 12 may be configured with preset treatment protocol programs (e.g. stored in the memory of the control unit), which can then be either selected, using a user interface (such as buttons or a touch screen as noted) or using a remote device.

In one aspect, a therapeutic device is disclosed for treating damaged tissue comprising a heating component; wherein heat can be applied to a limb. In another embodiment, the therapeutic device includes a plurality of electrodes, wherein at least one electrode supplies electrical pulse stimulation. The therapeutic device, in some embodiments, further includes a plurality of sensors, wherein at least one sensor is configured to measure indicators of wound healing. In another embodiment, a pulse generator is electrically coupled with the plurality of electrodes, wherein the pulse generator is configured to generate a plurality of electrical impulses for delivering electrical stimulation treatment to a subject through at least one electrode. The therapeutic device for treating damaged tissue in some embodiments, includes at least one control unit to operate the electrical pulse stimulation and the heating component. In other embodiments, the therapeutic device includes a processor, wherein the processor includes processing logic and telemetry to determine the optimal treatment regimen for maximizing blood flow based on carry-over effects (that is when the effect of the treatment continues after the treatment is stopped).

In a second aspect, disclosed is a method of treating damaged tissue comprising the steps of: identifying tissue to be treated; placing a therapeutic device; selecting a treatment protocol; applying heat to a limb comprising the identified tissue; simultaneously conducting an electrical current through the plurality of electrodes; using a plurality of sensors to record stimulation data and indicators of wound healing during treatment and after treatment, wherein the indicators are physiological, such as bioimpedance, pH, heat and periwound measurements; enabling, disabling, and altering the electrical stimulation and heat based on the recorded indicators; and determining future treatment parameters based on the recorded indicators.

In a third aspect, this invention includes a system for treating damaged tissue comprising a processing device. In one embodiment, a non-transitory computer-readable medium communicatively coupled to the processing device, wherein the processing device is configured to perform operations. In some embodiments, the operations of the system include: receiving a data set associated with patient indicators of wound healing and stimulation data; storing the data set; generating treatment parameters based on the stored data by determining a relationship between initial treatment parameters and plurality of the indicators of wound healing and the stimulation data; electronically converting the stored data into the next parameters based on the relationship; and generating an interface for display that includes data associated with the indicators of wound healing and the stimulation data.

Each of the embodiments of the disclosed devices, methods, and systems allow for the rapid healing of damage tissue, such as wounds. For example, the disclosed devices, methods, and systems can promote healing of ulcers, such as diabetic foot ulcers (DFUs), in a shortened time period with superior results.

In some embodiments, the invention can be used to treat damaged cells including, but is not limited to ulcerated tissue. In addition to ulcers (such as DFUs), this device can be used to treat other damage tissue, such as arthritic tissue, tendonitis, tendon or ligament damage, muscle soreness, joint pain, varicose veins, obesity, and peripheral artery disease.

Additionally, the device can promote the healing of xenograft, allograft, autograft, or engineered tissue following reconstruction surgery. Wounds that can be treated by the present invention include, but are not limited to non-healing or chronic wounds. In some embodiments a wound that does not improve after at least 3, 4, or 5 weeks or does not heal after at least 7, 8, or 9 weeks are non-healing wounds. Non-healing wounds include, but are not limited to DFUs, venous-related ulcerations, non-healing surgical wounds, pressure ulcers, wounds related to metabolic disease, and wounds that repeatedly break down. Non-healing wounds place patients at an increased risk for infections. Often, poor-healing, neuropathic wounds that occur on diabetic patients, especially on the lower extremities, will only worsen if left untreated. Patients who have diabetes experience reduced blood flow and nervous activity in the limbs, and ulcers often begin in high pressure areas, such as on the bottom of the foot.

Device for the Treatment of Damaged Tissue

In one embodiment, a therapeutic device for treating damaged tissue includes: a heating component; wherein heat can be applied to a limb; a plurality of electrodes, wherein at least one electrode supplies electrical pulse stimulation; a plurality of sensors, wherein at least one sensor is configured to measure indicators of wound healing; a pulse generator being electrically coupled with the plurality of electrodes, wherein the pulse generator is configured to generate a plurality of electrical impulses for delivering electrical stimulation treatment to a subject through at least one electrode; at least one control unit to operate the electrical pulse stimulation and the heating component; and a processor, wherein the processor includes processing logic and telemetry to determine the optimal treatment regimen for maximizing blood flow based on carry-over effects.

In some embodiments, the heating component is a flexible internal heating coil. The therapeutic device, in some embodiments includes a plurality of layers comprising a heating component layer having a first side and second side; an inner layer comprising a plurality of dissimilar materials, wherein the inner layer contacts the subject's skin; an outer layer comprising a plurality of dissimilar materials; and a discontinuous adhesive layer which affixes the first side of the heating layer to the inner layer and the second side of the heating component layer to the outer layer. In some embodiments, the inner layer includes two or more sublayers.

Also in some embodiments, a first sublayer is an inner insulative sublayer, wherein the inner insulative sublayer is an absorbent polymer. In further embodiments, the insulative sublayer contacts the subject's skin. The inner insulative sublayer, in some embodiments, includes at least one of fleece, wool, cotton, nylon, polyester, or a combination thereof. The inner insulative sublayer can be coated with an anti-microbial material. In further embodiments, a second sublayer is an inner conductive sublayer, wherein the inner conductive sublayer is an organic polymer. The organic polymer may include at least one of polyethylene terephthalate (PET), metallized polyethylene terephthalate (MPET), or biaxially oriented PET (BoPET).

In another embodiment, the skin contacting layer may comprise a thermally conductive gel, including a thermally conductive gel adhesive, such as HYRDROGEL.

The inner layer may uniformly distribute heat over the whole limb or sections thereof. In further embodiments, the thickness of the inner layer may be from 1-50 mm, or from 2-25 mm, or from 5-10 mm.

Also in some embodiments, the outer layer includes two or more sublayers. A first outer sublayer may include a plastic mesh layer, wherein, the plastic mesh layer contacts the second side of the heating component layer. A second outer sublayer may include a synthetic rubber. In some embodiments, the synthetic rubber includes at least one of neoprene, polyurethane, or nitrile rubber. Also in further embodiments, the thickness of the outer layer may be from 1-50 mm, or from 2-25 mm, or from 5-10 mm.

Sensors may be used to measure indicators of wound healing. The plurality of sensors in some embodiments, include at least one of Doppler probes, Hall Effect probes, skin temperature probes, or a differential high voltage probe.

In some embodiments, the therapeutic device includes at least one control unit to operate the electrical pulse stimulation and the heating component. Also in some embodiments, the at least one control unit includes a thermostat for selecting an amount of energy to maintain the tissue temperature.

Figure 1C:
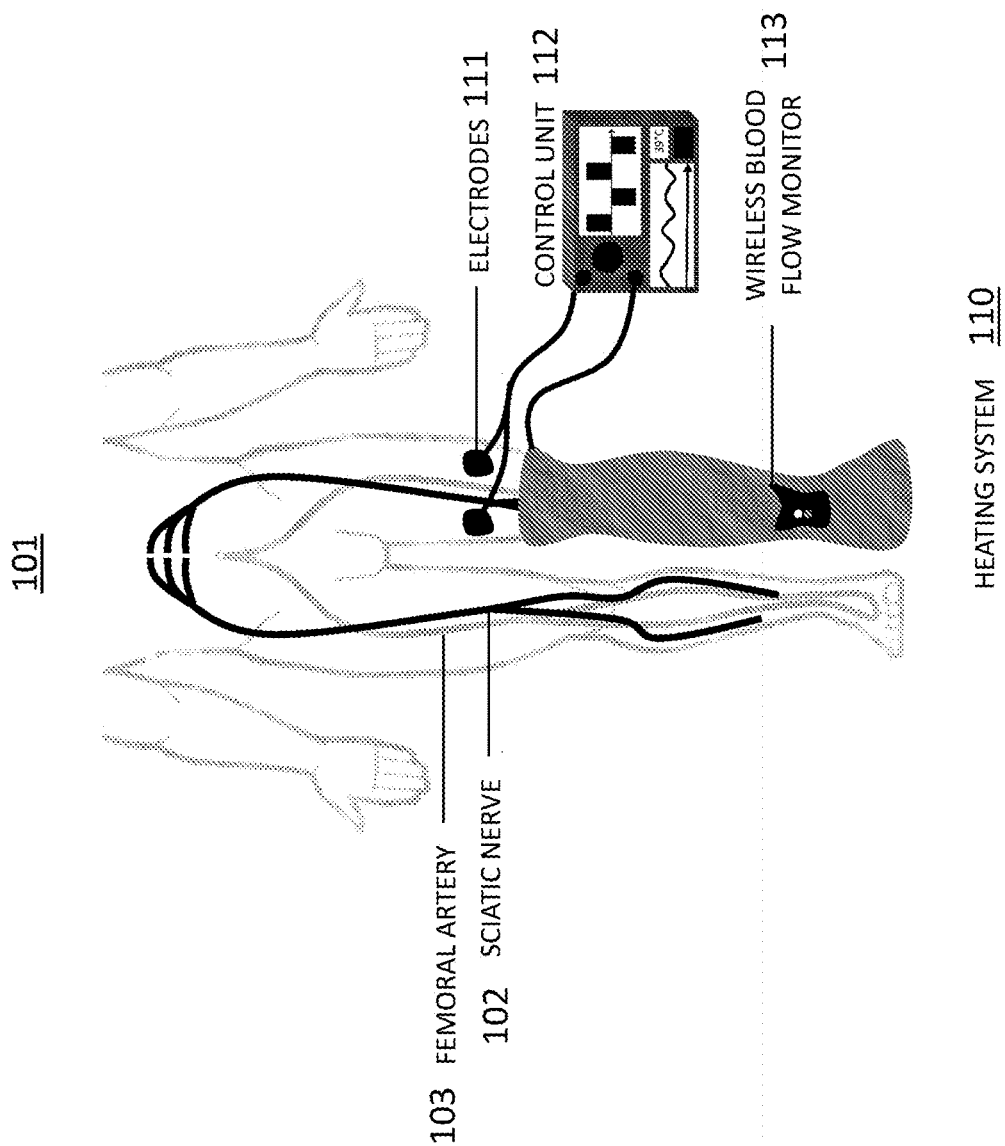
FIG. 1C is a schematic diagram illustrating another embodiment of the device for wound healing in accordance, which is capable of guiding electrode placement around a wound or a distal nerve, applying electrical stimulation, applying heat, and/or monitoring blood flow to control the treatment endpoint.

FIG. 1C illustrates an embodiment of a device 101 for treating damaged tissue using a thermo-regulated electrical stimulation. The therapeutic device may include a control unit 112 that controls a pulse generator, which can generate a plurality of electrical impulses for delivering the electrical pulse stimulation treatment to a subject through a plurality of electrodes 111. The device may further include a limb heating system 110, which globally applies heat to a limb that contains damaged tissue to be treated. In some embodiments, the electrodes 111 are placed on a skin surface in a general region of interest. The general region of interest may be a critical nerve and/or blood vessel. A wireless blood flow monitor 113 can be used to record physiologic measurements.

In some aspects, the invention may include a device for applying heat to the limb or a portion thereof. In some embodiments, heat is applied to the whole-limb. The whole-limb may be either a leg or an arm. In other embodiments, heat is applied to at least one section of the limb. The leg is composed of five distinct sections: upper leg, knee, lower leg, ankle and foot. The upper leg begins at the hip and continues down to the knee. The knee is a pivot-like hinge joint in the leg that connect the upper and lower leg. The lower leg begins at the knee and continues down to the ankle. The ankle connects the lower leg to the foot. In some embodiments, heat is applied to the lower leg-ankle-foot complex. In still other embodiments, heat is applied to at least the distal one-third of the lower limb, but is preferably applied to at least the distal two-thirds of the lower limb. As used here, distal means further away from the heart and proximal means closer to the heart. In other embodiments, the device may be used to treat wounds on the trunk of the body.

In some embodiments, the heating component is a flexible internal heating coil. A flexible heating component will generally allow the heating component to conform to a three-dimensional object. In some embodiments, the three-dimensional object may be a whole-limb or a portion thereof. In other embodiments, the flexible heating component may be a wearable garment, such as a boot, a sleeve for a shoulder, an elbow, or other body part.

In some embodiments, the heating component is internal to the device. In some embodiments, the heating component is removable. A removable heating component can be inserted into an opening between the inner and the outer layers. In other embodiments, the heating component will be fused into a single unit. In alternate embodiments, the thickness of the heating component layer may be from 1-20 mm, or from 1-10 mm, or from 1-5 mm.

In some embodiments, the heating component is run with a variable voltage supply. In alternate embodiments, the variable voltage supply may be from 1-120 V or from 1-24 V. A dry-cell battery can be used to generate heat by means of an electric current. In some embodiments, the battery will have a voltage capacity of 12 V.

In some embodiments, the device includes a plurality of layers comprising: a heating component layer having a first side and second side; an inner insulative layer comprising a plurality of dissimilar materials, wherein the inner insulative layer contacts the subject's skin; and an outer insulative layer comprising a plurality of dissimilar materials; and a discontinuous adhesive layer which affixes the first side of the heating layer to the inner layer and the second side of the heating layer to the outer layer. In some embodiments, an inner insulative layer includes two or more sublayers. In some embodiments, the first inner insulative sublayer is an absorbent polymer, wherein the first inner insulative sublayer contacts the subject's skin.

The first insulative sublayer may be a woven material, a non-woven material, or a fleece. In some embodiments, the inner insulative sublayer includes at least one of fleece, wool, cotton, nylon, polyester, or a combination thereof. In some embodiments, the insulating fabric can include a synthetic fleece. The synthetic fleece may be a nonwoven fabric made from polyester. In such an embodiment, the fleece may have a density between 50-500 g/m$^2$ or thickness may be from 1-20 mm, or from 1-10 mm or from 1-5 mm. In some embodiments, the first layer is fabricated so as to adhere poorly to wounds. In such embodiments, poor adhesion allows the device to be easily removed from the wound, enabling treatment with limited to no pain to the patient.

In some embodiments, an inner conductive sublayer is an organic polymer. In some embodiments, the organic polymer includes at least one of polyethylene terephthalate (PET), metallized polyethylene terephthalate (MPET), or biaxially oriented (BoPET, i.e., MYLAR®). PET is a thermoplastic polymer resin of the polyester family. PET can be spun into fibers for permanent-press fabrics, blow-molded, or extruded. MPET is a polymer film coated with a thin layer of metal. In some embodiments, the metal is aluminum. BoPET is a polyester film made from stretched PET. In other embodiments, an inner conductive sublayer may be graphite, copper, and silicon, and carbonaceous nanomaterials.

In some embodiments, the inner conductive sublayer is NASA foil. NASA foil is a MPET. NASA foil is a vacuum-metallized insulating material. NASA foil is designed to be lightweight, and may be made by depositing vaporized aluminum onto thin plastic substrates. The result is a thin, flexible material that provides superior thermal-reflective properties. The flexible nature of NASA foil allows it to conform to three-dimensional objects. In some embodiments, the three-dimensional object may be a whole-limb or portion thereof. In some embodiments, the three-dimensional object may be a wearable garment (e.g., a boot). In some embodiments, the thickness of the inner conductive layer is from 1-20 mm, or from 1-10 mm, or from 1-5 mm. In aspects of the invention, the inner layer uniformly distributes heat over the whole limb. NASA foil is ideal for equally distributing and retaining heat on treated areas of skin due to its superior thermal-reflective properties. In some instances, NASA foil is meant to conserve heat as a passive warming system and is able to stop both evaporative and connective heat loss.

In some embodiments, the outer layer includes two or more sublayers. In some embodiments, the first outer sublayer is a plastic mesh layer, wherein the plastic mesh layer contacts the second side of the heating component layer. In some embodiments, the second outer sublayer is a synthetic rubber. Synthetic rubbers have elastic properties that allow them to conform to a three-dimensional object. Such elasticity is ideal as it allows the device achieve optimal contact with the area of skin to be treated. In some embodiments, the synthetic rubber includes at least one of neoprene, polyurethane, or nitrile rubber. In some embodiments, the thickness of the outer layer is from 1-20 mm, or from 1-10 mm, or from 1-5 mm.

Figure 2:
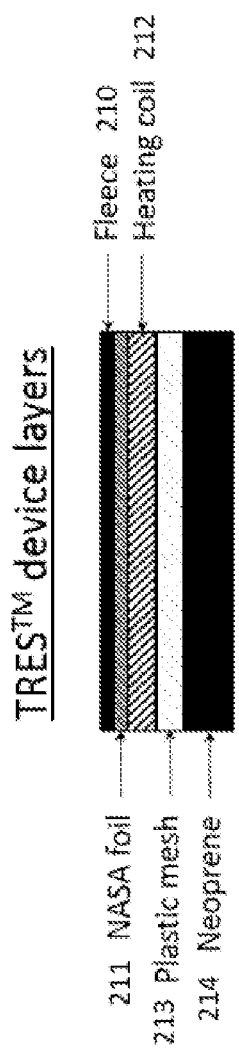
FIG. 2 is a schematic cross-section of the device of FIG. 1A.
Figure 2A:
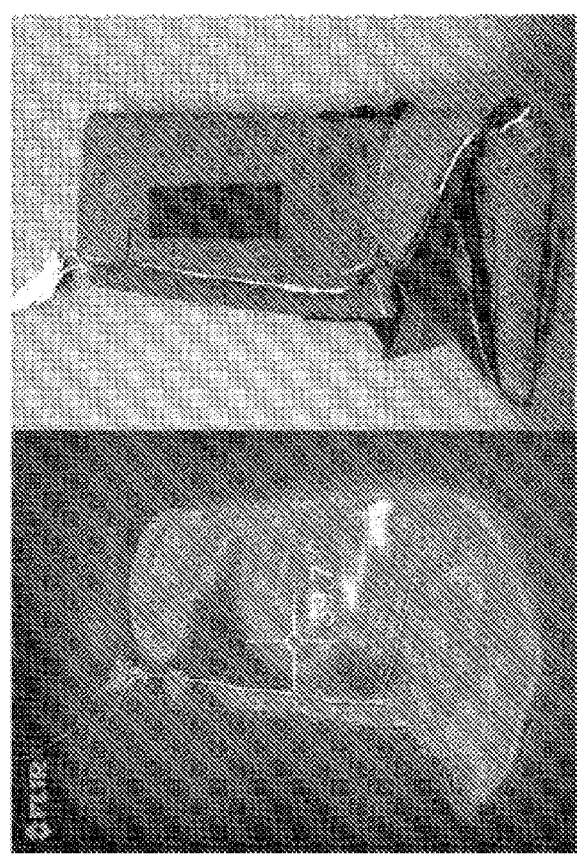
FIG. 2A is a side by side image of a thermal map (left (39.7° C. at crosshair)) of a prototype and an image of the prototype (right)

FIG. 2 illustrates an embodiment of the invention wherein the medical device includes 5 layers. The inner insulative sublayer is fleece 210 with a thickness of 0.5 cm. The inner conductive sublayer is NASA foil 211 with a thickness of 0.5 cm. The first outer insulative sublayer is plastic mesh 213 with a thickness of 2.0 cm. The second outer sublayer is neoprene 214 with a thickness of 1.0 cm. An internal heating coil 212 is inserted in between the inner conductive sublayer 211 and the first outer sublayer 213.

Sensors may be used to measure indicators of wound healing. In various embodiments, the plurality of sensors include at least one of Doppler probes, Hall Effect probes, skin temperature probes, and a differential high voltage probe. Doppler probes are capable of measuring blood flow. In some embodiments, a wide-band Hall Effect sensor is used to monitor current. Skin temperature probes are capable of monitoring the temperature of the skin at treated sites. Differential high voltage probes can record voltage in real-time.

The therapeutic device for treating damaged tissue in some embodiments includes at least one control unit to operate the electrical pulse stimulation and the heating component. In some embodiments the at least one control unit includes a thermostat for selecting an amount of energy to maintain the tissue temperature. A thermostat comprising a temperature control switch or button can be used in connection with a temperature control element of the heating component.

In further embodiments, the therapeutic device includes a processor, wherein the processor includes processing logic and telemetry to determine the optimal treatment regimen for maximizing blood flow based on carry-over effects.

Methods for the Treatment of Damaged Tissue

In another embodiment provided is a method of treating damaged tissue. The method may include the steps of identifying tissue to be treated; placing a therapeutic device on or around a limb encompassing the wound; selecting a treatment protocol; and applying heat and electrical stimulation to the limb and/or wound. The device may, in various embodiments include: a heating component; wherein heat can be applied to a limb; a plurality of electrodes, wherein at least one electrode supplies electrical pulse stimulation. The device may include a plurality of sensors, wherein at least one sensor is configured to measure indicators of wound healing. The device may also include a pulse generator being electrically coupled with the plurality of electrodes, wherein the pulse generator is configured to generate a plurality of electrical impulses for delivering electrical stimulation treatment to a subject through at least one electrode. The device may also include or be in communication with at least one control unit to operate the electrical pulse stimulation and the heating component; and a processor, wherein the processor includes processing logic and telemetry to determine the optimal treatment regimen for maximizing blood flow based on carry-over effects. In some embodiments, communication between at least one control unity and the device may be wireless. For example, the stimulation circuitry may be located within the device with an external trigger located within a control unit, wherein the control unit communicates wirelessly with the stimulation circuitry within the device. In certain embodiments, the method may include the steps of simultaneously conducting an electrical current through the plurality of electrodes; using a plurality of sensors to record stimulation data and indicators of wound healing during treatment and after treatment, wherein the indicators are physiologic and bio-impedance measurements. The method may include enabling, disabling, and altering the electrical stimulation and heat based on the recorded indicators; and determining future treatment parameters based on the recorded indicators. As discussed herein for devices, the methods may be applied to a whole limb or part of a limb.

Also disclosed herein are methods for treating damaged tissue wherein the device is placed around a limb. In some embodiments, the limb is a leg. In further embodiments, the device is placed around a leg or one or more sections thereof. Also disclosed herein are methods wherein the at least one control unit includes a thermostat for selecting an amount of energy to maintain the tissue temperature. The heating component may generate an amount of energy, which has been predetermined to maintain the tissue temperature from 45-300 C or from 40-35° C.

In some embodiments of the methods, the electrodes include two or more electrical conductors. The electrodes may be placed on a skin surface in a general region of interest. The general region of interest may include a critical nerve or blood vessel. In other embodiments, the general region of interest may include the area surrounding a critical nerve or blood vessel. Critical nerves, when stimulated, may assist with vasodilation of blood vessels thus increasing blood flow. Also in some embodiments, the critical nerve may be a vasoconstrictor nerve. In further embodiments, the vasoconstrictor nerve may be a sciatic nerve. In other embodiments, the nerve is a tibial or peroneal nerve. In other embodiments, the blood vessel is a femoral artery. In other embodiments, the general region of interest may be a wound. In some embodiments, electrodes may be placed to bracket the wound (e.g. placed on either side of wound).

Other aspects of the invention include methods for treating damaged tissue wherein a test pulse is delivered to determine the baseline electrical impedance of the tissue and ensure proper connectivity of the electrodes. The electrical pulses may be applied in an amount, which has been predetermined to cause vasodilation of blood vessels, wherein the electrical pulses may be applied for a pulse duration ranging from 1-5000 μs, or from 2-1,000 μs, or from 5-500 μs, or from 10-50 μs. In some embodiments, the electric pulses may have a voltage ranging from 0.1-500 V, or from 5-250 V, or from 50-100 V. In some embodiments, the electrical pulses may have a current amplitude ranging from 1-500 mA, or from 5-250 mA, or from 50-100 mA. In another embodiment, the electric pulses may have a voltage ranging from 0.1 to 200 V, or from 50 to 100 V, or from 0.1 to 50 V. In some embodiments, the electrical pulses may have a current amplitude ranging from 1-500 mA, or from 5-250 mA, or from 50-100 mA.

In other embodiments of the methods, the electrical pulses may be applied in an amount, which has been predetermined to cause nerve stimulation by using comparatively longer pulses or pulses of greater strength. In some embodiments, the electrical pulses may be applied for a duration ranging from 1-10000 μs, or from 2-5000 μs, or from 50-1000 μs, or from 100-500 μs. In some embodiments, the electric pulses may have a voltage ranging from 1-1500 V, or from 50-1000 V, or from 200-500 V. In another embodiment, the electric pulses may have a voltage ranging from 0.1-200 V, or from 0.1 to 50 V, or from 50-100 V. In some embodiments, the electrical pulses may have a current amplitude ranging from 1-1500 mA, or from 50-1000 mA, or from 200-500 mA.

In other embodiments, the electrical pulses may be applied in an amount, which has been predetermined to kill bacteria via non-thermal irreversible electroporation. In some embodiments, the electrical pulses may be applied for a duration ranging from 1-1000 μs, or from 1-750 μs, or from 2-500 μs. In some embodiments, the electric pulses may have a voltage ranging from 0.1-2000 V, or from 100-1500 V, or from 500-1000 V. In another embodiment, the electric pulses may have a voltage ranging from 0.1-300 V, or from 50-100 V, or from 0.1-50 V. In some embodiments, the electrical pulses may have a current amplitude ranging from 1-2000 mA, or from 100-1500 mA, or from 500-1000 mA.

A variety of waveforms can be used in electrical stimulation to target specific areas of the body. In some embodiments, a waveform of the electrical pulse stimulation includes at least one of biphasic, asymmetrical biphasic, polyphasic, and pulsed direct current (DC). Also in some embodiments, a current of the electrical pulse stimulation includes at least one of sawtooth, trapezoid, triangular, rectangular, spike, or sine.

In some embodiments of the methods for treating damaged tissue, the plurality of sensors include at least one of Doppler probes, Hall Effect probes, skin temperature probes, or a differential high voltage probe. In further embodiments of the methods, the recorded stimulation data includes at least one of current, waveform, voltage, and amplitude. The electrical stimulation pulses may be delivered in synchrony with the heart beat using sensor blood perfusion or electrical impedance measurements. The electrical pulses can be used to improve blood vessel compliance during systole.

The indicators of wound healing include at least one of blood perfusion, pH, temperature, electrical activity, electrical impedance, a chemical concentration, a gas amount, wound size, or combination thereof. Other aspects of the invention include methods for treating damaged tissue wherein the sensors measure the indicators of wound healing at various intervals after treatment. In some embodiments, indicators of wound healing may be measured post-treatment at 5 seconds, or 10 seconds, or 30 seconds, or 1 min, or 5 min, or 10 min, or 30 min, or 1 hour, or 3 hours, or 6 hours, or 12 hours, or 24 hours, or 36 hours, or 48 hours, or 72 hours, or 96 hours. In some embodiments, indicators of wound healing may be measured in real-time for the first hour after treatment ends. In some embodiments of the methods, the future treatment protocols are determined by the extent of a carry-over effect. The carry-over effect may include an effect lasting beyond a treatment application. Post-treatment measurements of indicators of wound healing can be used to determine the extent of a carry-over effect. Further embodiments of the methods include determining whether, after treatment, at least one of the physiologic measurements has returned to a range of values associated with a pre-treatment baseline, and initializing a subsequent treatment based on the determination. Still further embodiments of the methods include determining whether, during treatment, one of the physiologic measurements does not reach the range of values of at least one of the physiologic measurements associated with previous treatments, and altering the energy delivery of a current treatment protocol and the future treatment protocol. The physiologic measurements may include one or more indicators of wound healing. In some embodiments, if blood perfusion drops below a predetermined value, the device may be triggered through an automated feedback loop to start treatment.

In some embodiments of methods for treating damaged tissue, the energy delivery may be altered by changing the frequency, duration, or amplitude of the electrical pulse stimulation. In other embodiments, the energy delivery may be altered by changing the frequency or duration of the heating component. Also in some embodiments, blood perfusion or electrical impedance measurements may be compared to a predetermined value, and the therapeutic delivery may be altered until the measurements taken during the diseased state resemble the predetermined value.

Other aspects of the invention include methods for determining normalization of blood flow using correlation and matched filtering. These methods provide a means to compute the similarity of blood perfusion or electrical impedance measurements from a template normal state to an unknown diseased state (e.g., absence of dicrotic notch in blood flow waveform for diabetic patients). This enables one to determine the extent of blood flow normalization, which can be used to control the time course of treatment. In some embodiments, the extent of wound healing may be tracked based on feedback from sensor recordings. The user may be prompted to change the position of the electrodes based on the electrical impedance or other sensor recordings. In other embodiments, the user may be prompted to change treatment parameters associated with heat and/or electrical stimulation delivery. Further embodiments include determining whether, after treatment, one of the physiologic measurements has returned to a range of values associated with a pre-treatment baseline, and notifying the user. A subject may use an application to photograph the damaged tissue as treatment progresses. In some embodiments, photographs may be uploaded using an application. Uploaded photographs may be accessed by a clinician.

In some embodiments a patient computing device, housing a camera, may be used by the patient to take photographs. In another embodiment, the patient computing device is configured to send and/or receive wireless signals. In an embodiment, the patient computing device is a mobile telephone device, for example, a smartphone. In another embodiment, the patient computing device is a home computer or laptop computer. In another embodiments, the patient computing device is a tablet. In some embodiments, the patient computing device is configured to be connected to a camera by a physical connection, such as a wire or other connection for transmitting signals. In another embodiment, the patient computing device can send and/or receive wireless signals to and/or from the camera.

In some embodiments, the at least one control unit includes a thermostat for selecting an amount of energy to maintain the tissue temperature. The heating component preferably contains a means for controlling the heat generated by the heating components, such as a thermostat control. In some embodiments, the thermostat control can be set to discontinue heating upon the skin reaching a specified temperature. In some embodiments, the heating component generates an amount of energy, which has been predetermined to maintain the tissue temperature at 50° C. to 35° C. In preferred embodiments, the temperature range will be constantly maintained in order to lower impedance and increase conductance of stimulation. Tissue impedance varies throughout the body and conductivity depends on the water content of tissue. High water content decreases impedance and improves conductance. Skin impedance is also inversely proportional to the temperature of the skin. Heat increases moisture content, which promotes conductivity. Temperature affects the impedance of the skin, with reduced impedance at increasing cutaneous temperatures.

Heating components can be run with a variable voltage supply. The voltage supply may be from 1-120 V, or from 1-60 V, or from 1-24 V. In some embodiments electrical stimulation may be used for both electric field generation and heating (low-voltage, long pulses may be used to obviate the need for a separate heating component).

In some embodiments, the control unit for electrical stimulation can manipulate variables comprising at least one of waveform, pulse duration, pulse width, and intensity.

In some embodiments, the electrodes include a plurality of electrodes. A plurality of electrodes is any number greater than 1, optionally at least 2, or at least 3, or at least 4, or at least 5, or at least 6. In one embodiment, the electrodes include two or more electrical conductors.

In some embodiments, the electrodes are placed on a skin surface in a general region of interest. The general region of interest may be a critical nerve and/or a blood vessel that supplies the damaged tissue. The human cutaneous circulation is controlled by sympathetic adrenergic vasoconstrictor nerves that coexist with sympathetic vasodilator nerves, a less well understood system that is activated during increased heat. Sympathetic vasoconstrictor and vasodilator nerves innervate all areas of nonglabrous skin, whereas areas of glabrous skin (palms, soles, lips) are innervated only by sympathetic vasoconstrictor nerves. In some embodiments, the critical nerve is a vasoconstrictor nerve. In further embodiments, the vasoconstrictor nerve is a sciatic nerve.

Physiologic measurements (e.g., blood flow) can be used in real-time to guide electrode placement, monitor wound healing, and serve as control inputs to the device. These measurements could include temperature, bioimpedance, photoplethysmography, and Doppler flow via laser or musculoskeletal ultrasound. In some embodiments, the device is capable of guiding electrode placement around the wound or distal nerve. Electrode placement must be specific over an area of high water content for optimal stimulation. In some embodiments, placement on a skin surface in a general region of interest is preferred.

The general region of interest in some embodiments is a nerve. The intracellular components of nerve and muscle have high water contents of 70% to 75%. Tissue impedance varies throughout the body and conductivity depends on the water content of tissue. High water content decreases impedance and improves conductance.

In general, the control of the circulation of the skin can be divided into two types: (1) the local response, which consists of vasodilation or vasoconstriction of vascular endothelial cells caused by metabolites and local pressure, heat, or shear stress on the blood vessel wall, and (2) central or global control, which consists of neurogenic control of vasolidation/vasoconstriction by the hypothalamus in response to skin surface temperature receptors. In Type-I and Type-2 diabetes, vasodilation is impaired through direct damage to endothelial cells. In some embodiments, the blood vessel is a femoral artery 103.

In some embodiments, a test pulse is delivered to determine a baseline electrical impedance of the tissue and ensure proper connectivity of the electrodes. Impedance is the opposition to current flow to the body. Electrodes are placed and a test is run to determine if the electrode placement permits sufficient current delivery to the nerve or wound. At this point, a treatment session of electrical stimulation can be started and may continue until blood flow ceases to increase for a threshold amount of time. In some embodiments, the threshold amount of time is from 1-30 min, or from 1-15 min, or from 2-5 min. If blood flow ceases to increase, alternate parameters (stimulation waveform, heat level, etc.) may be administered.

The electrical pulses may be applied in in an amount, which has been predetermined to cause vasodilation of blood vessels, wherein the electrical pulses may be applied for a duration ranging from 1-5000 µs, or from 2-1,000 µs, or from 5-500 µs, or from 10-50 µs. In some embodiments, the electric pulses may have a voltage ranging from 0.1-500 V, or from 5-250 V, or from 50-100 V. In another embodiment, the electric pulses may have a voltage ranging from 0.1-200 V, or from 50-200 V, or from 100-200 V. In some embodiments, the electrical pulses may have a current amplitude from 1-500 mA, or from 5-250 mA, or from 50-100 mA.

In other embodiments of the methods, the electrical pulses may be applied in an amount, which has been predetermined to cause nerve stimulation by using comparatively longer pulses or pulses of greater strength. In some embodiments, the electrical pulses may be applied for a duration ranging from 1-10000 µs, or from 2-5000 µs, or from 50-1000 µs, or from 100-500 µs. In some embodiments, the electric pulses may have a voltage ranging from 0.1-1500 V, or from 50-1000 V, or from 200-500 V. In another embodiment, the electric pulses may have a voltage ranging from 0.1-200 V, or from 50-200 V, or from 100-200 V. In some embodiments, the electrical pulses may have a current amplitude from 1-1500 mA, or from 50-1000 mA, or from 200-500 mA.

In other embodiments, the electrical pulses may be applied in an amount, which has been predetermined to kill bacteria via non-thermal irreversible electroporation. Non-healing wounds place patients at an increased risk for infections from common bacteria found on the skin and in the environment. In some embodiments, the electrical pulses may be applied for a duration ranging from 1-1000 µs, or from 1-750 µs, or from 2-500 µs. In some embodiments, the electric pulses may have a voltage ranging from 0.1-2000 V, or from 100-1500 V, or from 500-1000 V. In another embodiment, the electric pulses may have a voltage ranging from 0.1-300 V, or from 50-300 V, or from 100-300 V. In some embodiments, the electrical pulses may have a current amplitude from 1-2000 mA, or from 100-1500 mA, or from 500-1000 mA.

Also, in some embodiments, the waveform of the electrical pulse stimulation includes at least one of monophasic, biphasic, asymmetrical biphasic, polyphasic, or pulsed direct current (DC) or other waveforms or types and combinations of currents may be used. In some embodiments, the current of the electric pulse stimulation includes at least one of sawtooth, trapezoid, triangular, rectangular, spike, or sine.

Figure 3:
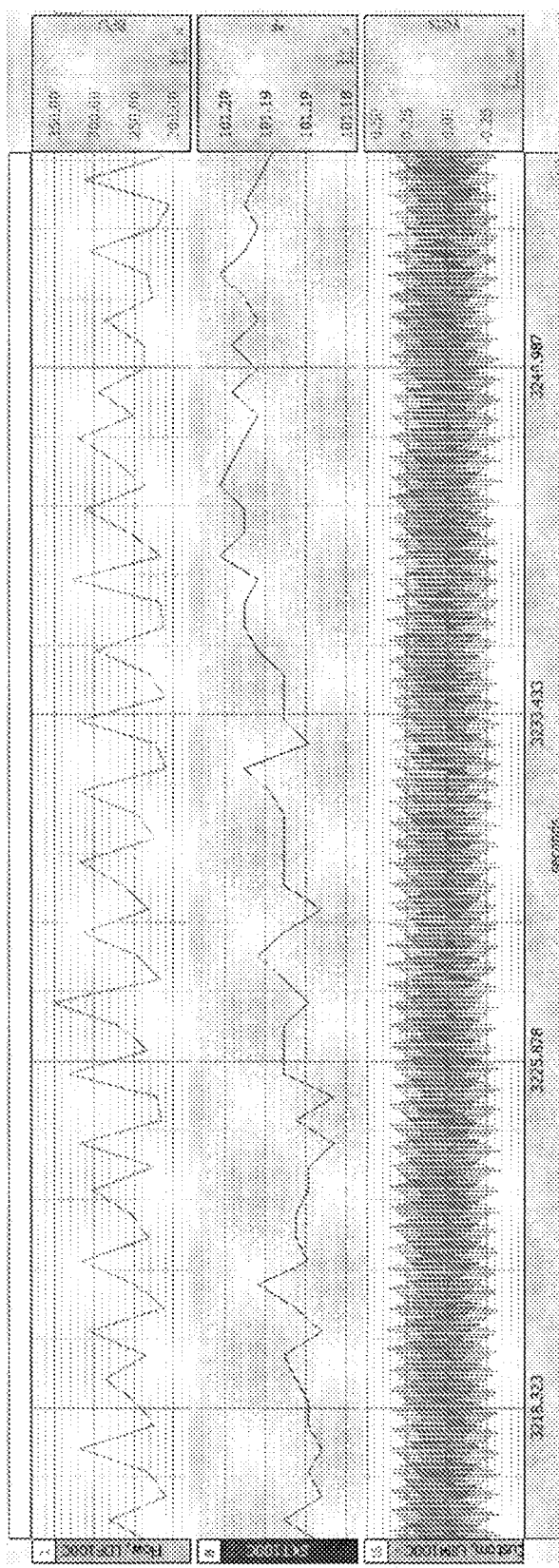
FIG. 3 shows a data display of a healthy human subject with 15 mA of electric stimulation in accordance with an embodiment of the disclosure (blood flow (top), skin temp (middle), and stimulation waveform (bottom))

In some embodiments, the recorded stimulation data may include amplitude, waveform, current, voltage, and amount of energy. FIG. 3 illustrates a display of stimulation data. For example, such stimulation data may include: blood flow (301), skin temperature (302), and stimulation waveform (303) or other parameters may be quantified.

Also, in some embodiments, electrical stimulation pulses may be delivered in synchrony with the heart beat using sensor blood perfusion or electrical impedance measurements.

In some embodiments, the electrical stimulation pulses can improve blood vessel compliance during systole. A photoplethysmography (PPG) signal from a normal patient has several characteristic features, including a systolic peak, dicrotic notch, and diastolic peak. Reduced blood vessel compliance is often observed in diabetes, and congestive heart failure can result in shortening of the time between the systolic and diastolic peaks. Additionally, this reduction can effectively mask the dicrotic notch. In some embodiments, the methods, systems, and devices can be configured to increase blood vessel compliance during systole. This can be performed by delivering electrical stimulus in synchrony with the heartbeat.

In some embodiments, a plurality of sensors include at least one of Doppler probes, Hall Effect probes, skin temperature probes, and a differential high voltage probe, or other sensors may be used. For example, one method of monitoring blood flow is to use a Doppler blood flow ultrasound monitor where a collar is wrapped around or adjacent to the junction of two vessel ends and a small sensor element that is a part of the collar is connected by fine wires to a benchtop or bedside monitor.

In some embodiments, a wide-band Hall Effect sensor is used to monitor current. A Hall effect sensor is a transducer that varies its output voltage in response to a magnetic field. Hall effect sensors are used for proximity switching, positioning, speed detection, and current sensing applications.

Skin temperature probes are capable of monitoring the temperature of the skin at treated sites. In some embodiments, the skin temperature probes are capable of continuous temperature monitoring.

Differential high voltage probes can record voltage in real-time. Differential high voltage probes can be used to measure the voltage difference between two test points.

The human skin has an impedance to an alternating current of low frequency, but this impedance decreases as frequency of the alternating electric current increases. Three separate branches of the sympathetic nervous system control skin blood flow: adrenergic vasoconstrictor nerves that reduce (constrict) skin blood vessels, and cholinergic and nitrogenic nerves that cause vasodilation of blood vessels by releasing the neurotransmitters, acetylcholine, nitric oxide or Substance P. In some embodiments, electrical stimulation can be directed at a specific nerve to enhance the production of acetylcholine, Substance P or nitric oxide (NO). In other embodiments, the indicators of wound healing are blood perfusion, pH, temperature, electrical activity, electrical impedance, a chemical concentration, a gas amount, wound size, or combinations thereof.

In some embodiments, the sensors measure the indicators of wound healing at various intervals after treatment. These measurements can be used to quantify the long lasting effects of treatment, including but not limited to, carry-over effects. Simultaneously delivering heat and electrical stimulation creates a synergistic effect on blood flow resulting in carry-over effects that persist after delivery of the energy. In some embodiments, the carry-over effects are long-lasting physiological changes. These physiologic changes may include, but are not limited to, changes in blood perfusion, pH, temperature, electrical impedance, a chemical concentration, a gas amount, or a wound size. In some embodiments, the method may include the following steps: determining whether after treatment, one of the physiologic measurements has returned to a range of values associated with a pre-treatment baseline and initializing a subsequent treatment. In some embodiments, sensors are used to detect physiologic measurements during treatment and after treatment. In some embodiments, measurements may be collected continuously and analyzed remotely in real-time. Physiologic measurements can be detected at least 5 min, or at least 10 min, or at least 15 min, or at least 30 min, or at least 1 hour, or at least 2 hours, or at least 5 hours, or at least 10 hours, or at least 24 hours, or at least 36 hours, or at least 48 hours, or at least 72 hours following treatment. In some embodiments, physiologic measurements may be detected at multiple time points following treatment.

Over time, a change in the responsiveness of the sensory system to a stimulus may occur. Thus, in some embodiments, the methods further include determining whether during treatment, one of the physiologic measurements does not reach the levels associated with previous treatments. This may be due to stimulus adaptation. The method may then include the step of altering the energy delivery of the current treatment. For example, when a specific treatment protocol fails to produce a similar physiologic response, the treatment protocol for the current treatment session can be altered until a similar physiologic response can be produced. Additionally or alternatively, the treatment protocol for future treatment sessions can be altered to achieve a physiologic response that reaches levels associated with current and/or previous treatment sessions.

In some embodiments, the energy delivery is altered by changing the frequency, duration, or amplitude of the electrical pulse stimulation. In some embodiments, stimulation parameters of higher frequency can be used.

There are several temperature regulatory systems the body uses to maintain stable body temperatures (homeostasis). The skin uses a complex control system to respond to local stimuli such as pressure and heat, to dissipate or save heat, and to maintain blood pressure with changes in body position. Sufficient intensity of and exposure to a stimulus is needed for activation of the temperature regulating center in the hypothalamus within the brain. The hypothalamus acts as the "body's thermostat" to maintain a normal range of human body temperature from 36° C. to 38° C. When sensory information reaches the hypothalamus, the information is integrated and interpreted along with information on the temperature of the blood circulating through the hypothalamus.

In some embodiments, the energy delivery is altered by changing the frequency or duration of the heating component. Elevating the tissue temperature can result in an increase in blood flow to the area, which is attributable in part to the vasodilatory response in surface blood vessels. The increase in blood flow; however, may remove heat from the area, whereas blood that is relatively cooler flows into the area, preventing excessive heat accumulation. Thus in some instances, therapeutic heating levels may not be reached because the increased blood flow may not allow for adequate heat build-up in the area. Heat accumulation is affected by the intensity and duration of the stimulus, as well as the rate of heat absorption by the tissue. In some embodiments, increased levels of heat must be provided to cause the hypothalamus to increase blood flow to the area.

In some embodiments, the blood perfusion or electrical impedance measurements are compared to a predetermined value, and the therapeutic delivery is altered until the diseased state resembles the predetermined value. In some embodiments, the predetermined value if that found in normal (i.e., non-wounded) tissue at the same site (i.e. place on limb). In some embodiments, cross-correlation is used to correlate blood perfusion or electrical impedance measurements from a template normal state to an unknown diseased state. The cross-correlation function is maximized when two signals have similar phase and frequency content.

In some embodiments, methods further include tracking the extent of wound healing based on feedback from sensor recordings. Examples of active feedback systems for monitoring blood flow include, but are not limited to impedance spectroscopy, photoplethysmography (PPG), or laser of ultrasound Doppler.

In some embodiments, the methods include the steps of determining the future treatment parameters by the extent of carry-over. Treatment with heat, increases blood flow initially, but eventually levels off. For example, addition of electrical stimulation may create a carry-over effect. Carry-over effects refer to long-lasting physiological changes following energy delivery. To date, the mechanism of the carry-over effects is unknown. The system and devices may utilize feedback from sensors to exploit carry-over effects and optimize wound healing. The optimal treatment protocol should maintain an improved physiologic measurement (e.g., increased blood flow) with the minimum number of treatments by coordinating energy delivery with the cessation of carry-over effects.

In some embodiments, the method may include prompting a subject to change the position of the electrodes after determining whether one of the physiologic measurements has returned to a range of values associated with a pre-treatment baseline, and notifying the user.

Also, in some embodiments, an application may be used to photograph and monitor ulcer size, allowing treatments to be administered at home. An application may be used to transmit information about wound healing to the clinician via pictures. For example, to monitor wound healing and track compliance, patients may use the WoundMAP app for measuring ulcer dimensions with a cellular device. Patients may also take 10 second video recordings of their wound, and the clips may be processed in MATLAB (Natick, Mass., USA) using a custom Eulerian Video Magnification script for visualizing changes in skin blood flow. Or other methods to visually record the wound may be used.

Systems for the Treatment of Damaged Tissue

Also disclosed herein are systems that employ the methods and devices described herein. The system may include various components. For example, the system may include a processing device, a non-transitory computer-readable medium communicatively coupled to the processing device, wherein the processing device is configured to perform operations comprising receiving a data set associated with patient indicators of wound healing and stimulation data. The processing device may also be configured to store the data set; generate treatment parameters based on the stored data by determining a relationship between initial treatment parameters and plurality of the indicators of wound healing and the stimulation data. The processing device may also be configured to electronically convert the stored data into the next parameters based on the relationship. The processing device may also be configured to generate an interface for display that includes data associated with the indicators of wound healing and the stimulation data.

Figure 5:
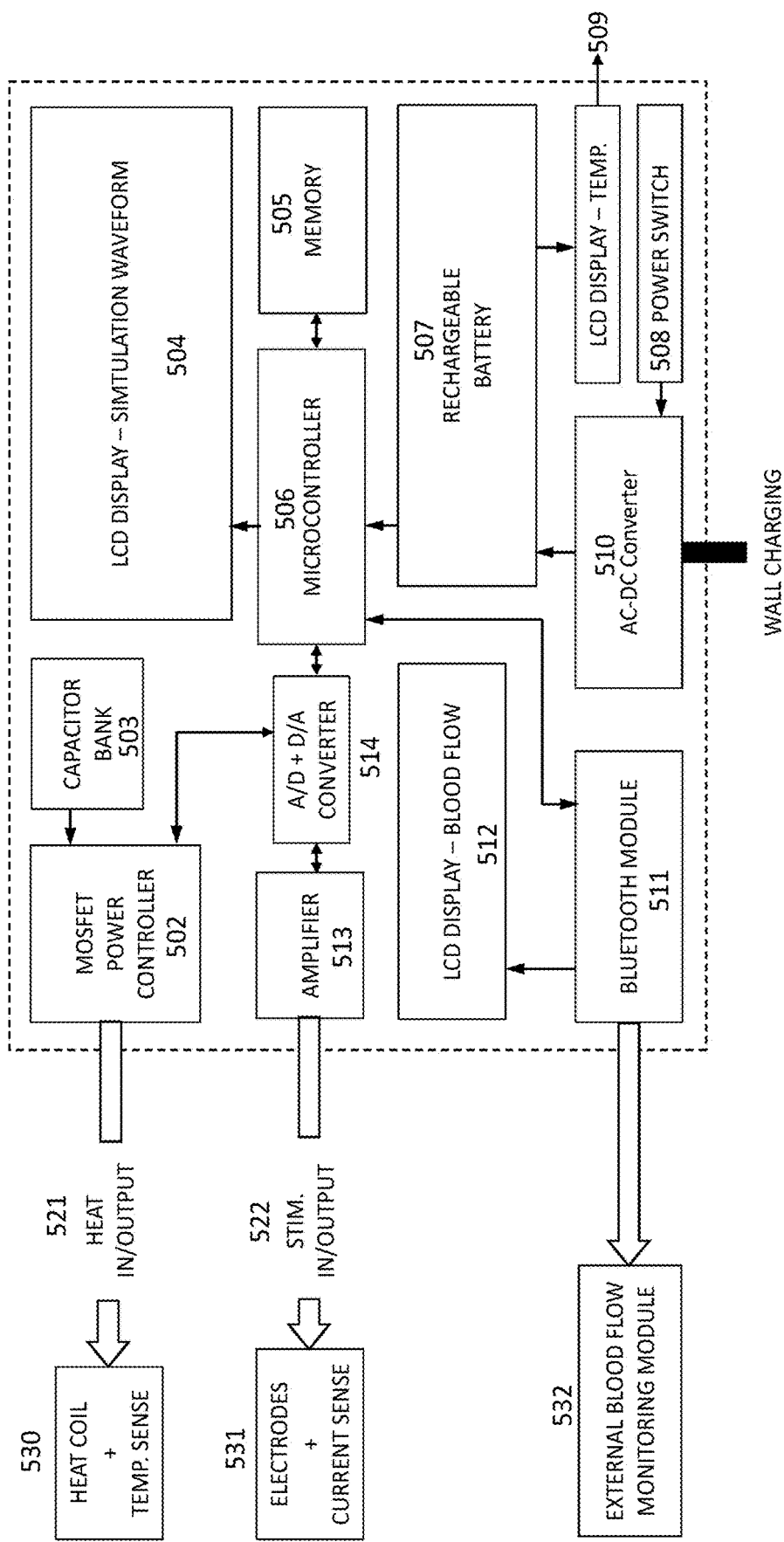
FIG. 5 shows a block diagram illustrating a control unit in accordance with an embodiment of the disclosure.
Figure 6:
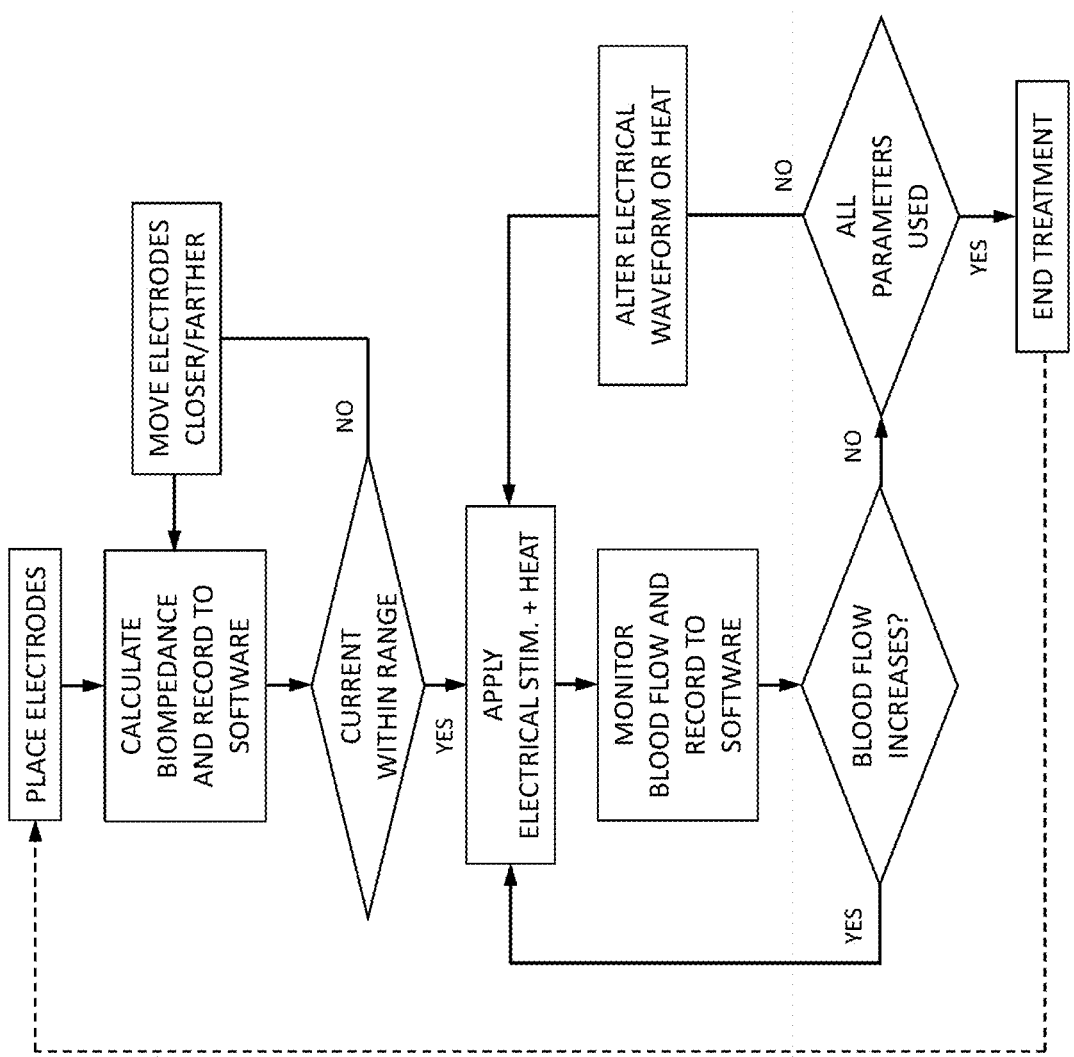
FIG. 6 shows a flow chart illustrating the decision tree based on physiologic measurement feedback in accordance with an embodiment of the disclosure.

FIG. 5 illustrates an embodiment of a control unit of a system 501 as disclosed herein. The system includes a power switch 508 coupled to a microcontroller 506 and an AC-DC converter 510, which is a type of external power supply that may supply power to a rechargeable battery 507. The microcontroller 506 may be a computer on a single integrated circuit and may include one or more CPUs, memory, and programmable input/output peripherals. In some embodiments, an analog-to-digital converter (AID) 514 is used to read analog sensors that can produce an analog sensor and convert the data to a digital signal that can be recognized by the microcontroller 506. The digital to analog converter (D/A) may allow the microcontroller 506 to output analog signals or voltage levels.

The microcontroller may be interfaced (in electrical communication) with an LCD display 504 capable of displaying electrical stimulation waveform. The output terminal of the amplifier 513 may be connected to the electrodes 531. In this way, the amplifier and associated circuitry can act as a voltage follower with unity gain and provide a high input impedance at the terminal.

The output terminal of the MOSFET Power Controller 502 may be connected to the heat coil 530. A power MOSFET is a specific type of metal oxide semiconductor field-effect transistor. MOSFETs are designed to handle significant power levels. In other embodiments, the power semiconductor device may be an insulated-gate bipolar transistor (IGBT). The power MOSFET 502 is a low-voltage (less than 200 V).

The Bluetooth module 511 is a wireless technology for exchanging data over short distances from fixed and mobile devices. The Bluetooth module may be configured to exchange data with the external blood flow monitoring module 532. The data collected from the external blood flow monitoring module 532 can be displayed on the LCD display 512.

Computer Systems and Computer Readable Media

In certain embodiments, the invention may include a system. The system may include at least some of the devices of the invention. Also, the system may include at least some of the components for performing the method. In other embodiments, the invention includes software for use with the methods or systems.

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may include a computer, an input device, a display unit, and/or the Internet. The computer may further include a microprocessor. The microprocessor may be connected to a communication bus. The computer may also include a memory. The memory may include random access memory (RAM) and read only memory (ROM). The computer system may further include a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device, which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may include, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may include a single type of computer-readable medium such as random access memory (RAM). In other embodiments, the computing device may include two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment includes a processor, which is configured to execute computer-executable program instructions and/or to access information stored in memory. The instructions may include processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device includes a single processor. In other embodiments, the device includes two or more processors. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device includes a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may include two or more network interfaces for communication over one or more networks. In some embodiments, the computing device may include a data store in addition to or in place of a network interface.

Some embodiments of suitable computing devices may include or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

EXAMPLES

The following examples describe methods of treatment with a shortened healing time and are to illustrate but not limit the invention.

Example 1. Prototypic Therapeutic Device and Methods

Figure 4:
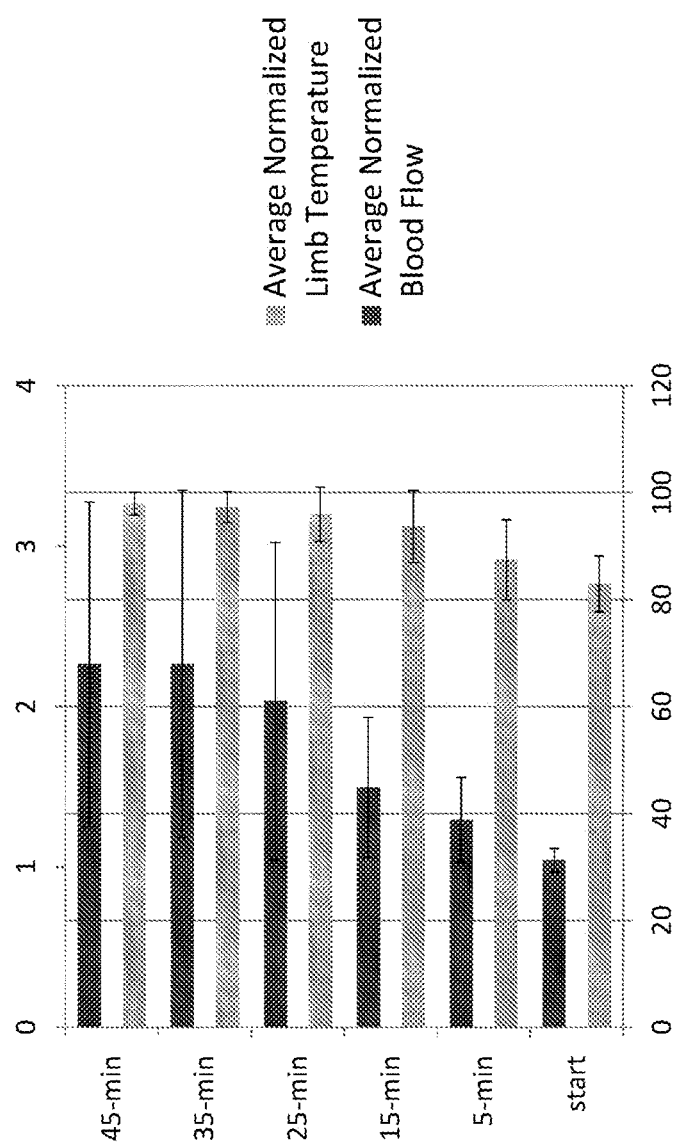
FIG. 4 shows supporting data from human subjects wearing the device in accordance with an embodiment of the methods (blood flow (blood perfusion units (BPU), black) doubles as temperature (° C., gray) increases)
Figure 7:
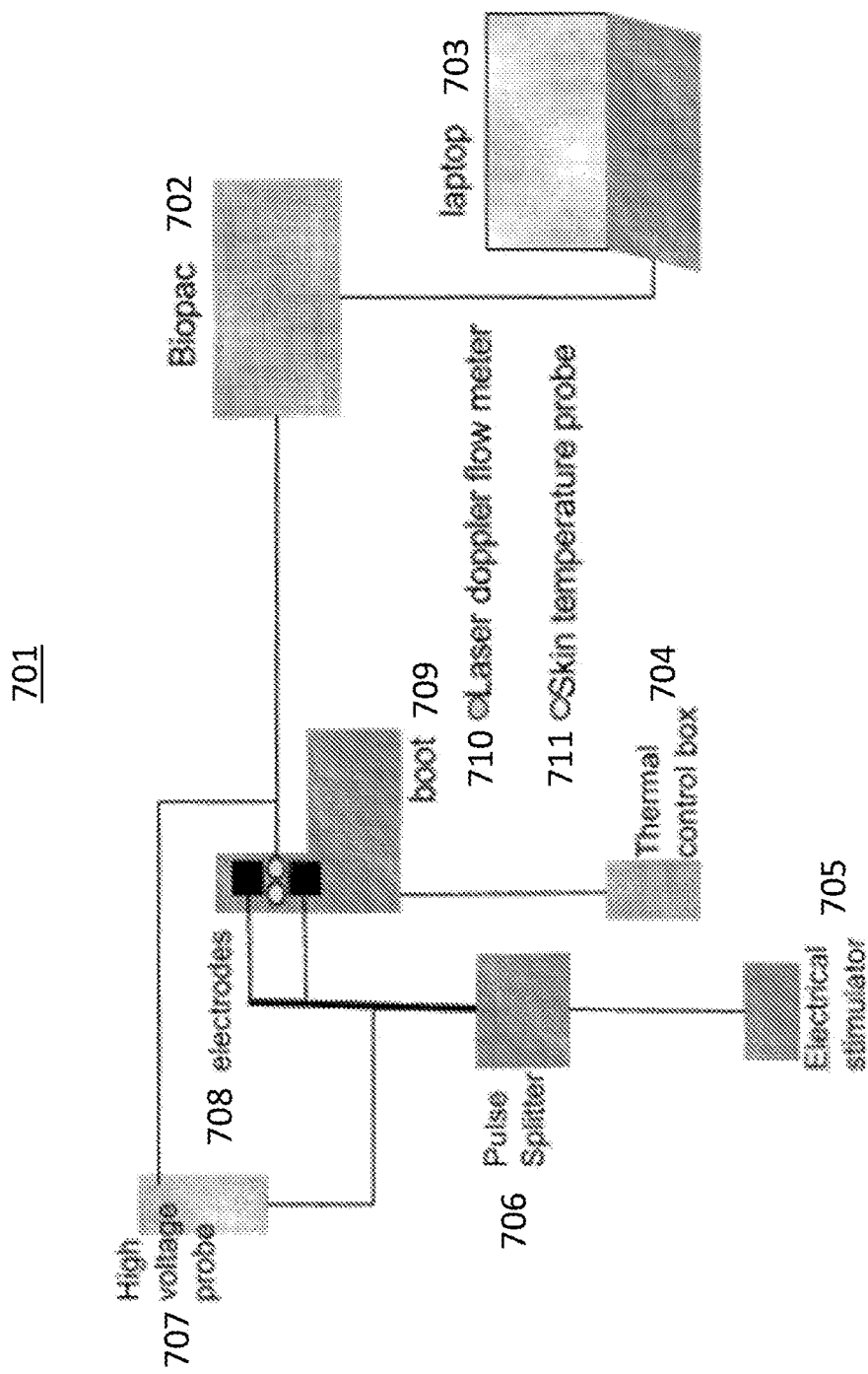
FIG. 7 shows an experimental setup used to acquire supporting data in accordance with an embodiment of the disclosure.

A prototype device was built as a stand-alone, at-home system for delivering heat and electrical stimulation to DFUs. An internal heating coil was encapsulated by several fabric layers to ensure uniform heating of the lower-limb (FIG. 2). Electrical stimulation was delivered using an external FDA approved device (EMPI continuum (continuum electrical stimulation device), St. Paul, Minn., USA), because it is capable of delivering a variety of pulse parameters. Under an approved IRB, four healthy subjects were tested. The heating component was set so that the skin temperature reached 37° C., and a symmetric, biphasic waveform was applied with currents reaching 20 mA. Data was acquired using a Biopac system (MP150, Goleta, Calif., USA) outfitted with a laser Doppler flow meter and skin temperature probe (FIG. 7). Additionally, a high voltage probe was used to record the output of the stimulator in real-time. A snapshot of the data (FIG. 3) shows traces for blood flow measured in blood perfusion units, skin temperature, and stimulator output voltage. By averaging over the course of the entire treatment, the results indicate that blood flow more than doubles while wearing the device (FIG. 4).

Example 2. Determining the Effects of Heat Alone on Healing of DFUs

The therapeutic device will be compared to a heating pad (2014-915 Xpressheat Heating Pad, Sunbeam, Boca Raton, Fla., USA) applied at the bottom of the foot with only vasoconstrictor nerves (typical location of DFU). Ten healthy subjects and ten subjects with Type-2 diabetes and no wound will be recruited. On different days and at random, subjects will be instructed to either wear the therapeutic device or foot sole heating pad. The subjects will lie supine on an examination table. Blood flow will be monitored continuously in the soles of both feet using the MP150 data acquisition system (Biopac Systems, Inc., Goleta, Calif., USA) combined with two laser Doppler flow amplifiers (LDF100C) and two surface probes (TSD140) from Biopac Systems. Temperature will be monitored continuously at the skin surface in the soles of both feet using the MP150 combined with two skin temperature amplifiers (SKTI00C) and two surface probes (TSD202) from Biopac Systems. Each session will last 1 hour. The subjects will undergo 15 minutes of baseline recordings followed by 45 minutes of heating (three, 15 min increments of increasing temperature (32, 35, and 38° C.)). In this study, no electrical stimulation will be applied, so as to isolate the effects of heat alone applied in various configurations.

Example 3. Treatment of DFUs with the Therapeutic Device

The electrical stimulation waveform and electrode location will be tested with the therapeutic device, and the temperature will be set to maximize blood flow to the treated leg. Three groups of ten subjects with Type-2 diabetes will be recruited to test three different waveforms (biphasic, asymmetrical biphasic, pulsed DC) synthesized by the EMPI continuum stimulator. To record voltage in real-time during treatment, the stimulator output will be split between adhesive electrodes on the subject's foot and a differential high-voltage probe (DP-25, Pintek Electronics, New Taipei City, Taiwan) connected to the analog input of the MP150 acquisition system. Additionally, the current will be monitored using a wide-band Hall Effect sensor (2877, Pearson Electronics, Palo Alto, Calif., USA) connected to a secondary analog input. The pulse width will be fixed at 300 μs and the amplitude will be increased to the highest level at which the subject is comfortable. The subjects will undergo 15 minutes of baseline recordings followed by 15 minutes of stimulation with the electrodes located on the foot sole and 15 minutes with the electrodes located across the sciatic nerve.

Example 4. Treatment of Non-Healing Wounds with Therapeutic Device

Ten patients with Type-2 diabetes and a neuropathic wound to test them at-home will be recruited. Only patients with no wound healing for two months prior will be selected and serve as their own control. Prior to starting treatment, patients will receive an examination of the wound and training on how to use the therapeutic device with electrical stimulation. The heating parameters will be chosen based on the combination of parameters from Example 3 that maximize blood flow to the foot. Baseline measurements of blood flow, blood pressure, heart rate, and wound dimensions will be taken. Patients will be divided into two groups for therapeutic treatment on three or six days per week. To monitor wound healing and track compliance, patients will use the WoundMAP app for measuring ulcer dimensions with a cell phone. They will also take 10 second video recordings of their wound, and the clips will be processed in MATLAB (Natick, Mass., USA) using a custom Eulerian Video Magnification script for visualizing changes in skin blood flow. At the end of the four week period, patients will return to the clinic for repeat baseline measurements.

Accordingly, the device and methods described herein for the treatment of DFUs or other non-healing ulcers, can improve blood flow locally to the wound through various means of electrical stimulation and application of heat. A portable device, for at-home use, allows for increased treatment times/frequency, lowers costs, and greater efficiency.

The following number paragraphs list various combinations of features or steps described herein that may be used in the treatment of damage tissue:

A therapeutic device for treating damaged tissue comprising:
a heating component; wherein heat can be applied to a limb;
a plurality of electrodes, wherein at least one electrode supplies electrical pulse stimulation;
a plurality of sensors, wherein at least one sensor is configured to measure at least one indicator of wound healing;
a pulse generator electrically coupled with the plurality of electrodes, wherein the pulse generator is configured to generate a plurality of electrical impulses for delivering the electrical pulse stimulation treatment to a subject through at least one of the electrodes;
at least one control unit to operate the electrical pulse stimulation and the heating component; and a processor, wherein the processor comprises processing logic and telemetry to determine the optimal treatment regimen for maximizing blood flow based on carry-over effects.

The device of paragraph 1, wherein the heating component is a flexible internal heating coil.

The device of paragraph 1 wherein the device comprises a plurality of layers comprising:
a heating component layer having a first side and second side;
an inner layer comprising a plurality of dissimilar materials, wherein the inner layer contacts the subject's skin;
an outer layer comprising a plurality of dissimilar materials; and
a discontinuous adhesive layer, which affixes the first side of the heating layer to the inner layer and the second side of the heating component layer to the outer layer.

The device of paragraph 3, wherein the inner layer comprises two or more sublayers.

The device of paragraph 4, wherein a first sublayer is an inner insulative sublayer, wherein the inner insulative sublayer is an absorbent polymer, and wherein the inner insulative sublayer contacts the subject's skin.

The device of paragraph 5, wherein the inner insulative sublayer comprises at least one of fleece, wool, cotton, nylon, polyester, or a combination thereof.

The device of paragraph 4, wherein a second sublayer is an inner conductive sublayer, wherein the inner conductive sublayer is an organic polymer.

The device of paragraph 7, wherein the organic polymer comprises at least one of polyethylene terephthalate (PET), metallized polyethylene terephthalate (MPET), or biaxially oriented PET (BoPET).

The device of paragraph 5, wherein the first sublayer is coated with an anti-microbial material.

The device of paragraph 3, wherein the inner layer uniformly distributes heat over the whole limb.

The device of paragraph 3, wherein the thickness of the inner layer is from 1-50 mm or from 5-10 mm.

The device of paragraph 3 wherein the thickness of the heating component layer is from 1-20 mm or from 1-5 mm.

The device of paragraph 3, wherein the outer layer comprises two or more sublayers.

The device of paragraph 13, wherein a first outer sublayer is a plastic mesh layer, wherein, the plastic mesh layer contacts the second side of the heating component layer.

The device of paragraph 13, wherein a second outer sublayer is a synthetic rubber.

The device of paragraph 15, wherein the synthetic rubber comprises at least one of neoprene, polyurethane, or nitrile rubber.

The device of paragraph 3 wherein the thickness of the outer layer is from 1-50 mm, or from 2-25 mm, or from 5-10 mm.

The device of paragraph 1, wherein the plurality of sensors comprise at least one of Doppler probes, Hall Effect probes, skin temperature probes, or a differential high voltage probe.

The device of paragraph 1, wherein the at least one control unit comprises a thermostat for selecting an amount of energy to maintain the tissue temperature.

A method of treating damaged tissue comprising the steps of: identifying tissue to be treated;
placing around a limb, a therapeutic device comprising:
a heating component, wherein heat can be applied to the limb; a plurality of electrodes, wherein at least one electrode supplies electrical pulse stimulation;
a plurality of sensors, wherein at least one sensor is configured to measure indicators of wound healing;
a pulse generator electrically coupled with the plurality of electrodes, wherein the pulse generator is configured to generate a plurality of electrical impulses for delivering the electrical pulse stimulation treatment to a subject through at least one of the electrodes;
at least one control unit to operate the electrical pulse stimulation or the heating component; and
a processor, wherein the processor comprises processing logic and telemetry to determine the optimal treatment regimen for maximizing blood flow based on carry-over effects;
selecting a treatment protocol; applying heat to a limb;
simultaneously generating an electrical impulse through the plurality of electrodes;
using a plurality of sensors to record stimulation data and indicators of wound healing during treatment and after treatment, wherein the indicators are physiologic and bio-impedance measurements; and
enabling, disabling, altering the electrical impulse stimulation and heat based on the recorded stimulation data and the recorded indicators.

The method of paragraph 20, wherein the device is placed around a limb.

The method of paragraph 20, wherein the limb is a leg.

The method of paragraph 20, wherein the device is placed around a leg or one or more sections thereof.

The method of paragraph 20, wherein the at least one control unit comprises a thermostat for selecting an amount of energy to maintain the tissue temperature.

The method of paragraph 20, wherein the heating component generates an amount of energy which has been predetermined to maintain the tissue temperature from 45° C.-30° C. or from 40-35° C.

The method of paragraph 20, wherein the electrodes comprise two or more electrical conductors.

The method of paragraph 20, wherein the electrodes are placed on a skin surface in a general region of interest.

The method of paragraph 27, wherein the general region of interest is a critical nerve or blood vessel.

The method of paragraph 20, wherein the critical nerve is a vasoconstrictor nerve.

The method of paragraph 20, wherein the vasoconstrictor nerve is a sciatic nerve.

The method of paragraph 20, wherein the blood vessel is a femoral artery.

The method of paragraph 20, wherein a test pulse is delivered to determine the baseline electrical impedance of the tissue and ensure proper connectivity of the electrodes.

The method of paragraph 20, wherein the electrical pulses are applied in an amount which has been predetermined to cause vasodilation of blood vessels, wherein the electrical pulses are applied for a duration ranging from 10-50 μs, having a voltage ranging from 50-100 V, and with a current amplitude from 50-100 mA.

The method of paragraph 20, wherein the electrical pulses are applied in an amount which has been predetermined to cause nerve stimulation, wherein the electrical pulses are applied for a duration ranging from 50-500 μs, having a voltage in a range of 200-500 V, and with a current amplitude from 200-500 mA.

The method of paragraph 20, wherein the electrical pulses are applied in an amount which has been predetermined to kill bacteria via non-thermal irreversible electroporation, wherein the electrical pulses are applied for a duration ranging from 2-500 μs, and the pulses produce a variable AC voltage having a voltage ranging from 500-1000 V, and with a current amplitude from 500-1000 mA.

The method of paragraph 20, wherein a waveform of the electrical pulse stimulation comprises at least one of biphasic, asymmetrical biphasic, polyphasic, and pulsed direct current (DC).

The method of paragraph 20, wherein a current of the electrical pulse stimulation comprises at least one of sawtooth, trapezoid, triangular, rectangular, spike, or sme.

The method of paragraph 20, wherein the plurality of sensors comprise at least one of Doppler probes, Hall Effect probes, skin temperature probes, or a differential high voltage probe.

The method of paragraph 20, wherein the recorded stimulation data comprises at least one of current, waveform, voltage, and amplitude.

The method of paragraph 20, wherein the electrical stimulation pulses are delivered in synchrony with the heart beat using sensor blood perfusion or electrical impedance measurements.

The method of paragraph 20, wherein the electrical pulses improve blood vessel compliance during systole.

The method of paragraph 20, wherein the indicators of wound healing are blood perfusion, pH, temperature, electrical activity, electrical impedance, a chemical concentration, a gas amount, wound size, or combination thereof.

The method of paragraph 20, wherein the sensors measure the indicators of wound healing every six hours post-treatment.

The method of paragraph 20, wherein the future treatment protocols are determined by the extent of a carry-over effect.

The method of paragraph 43, wherein the carry-over effect is an effect lasting beyond a treatment application.

The method of paragraph 20, further comprising determining whether, aftertreatment, one of the physiologic measurements has returned to a range of values associated with a pre-treatment baseline, and initializing a subsequent treatment based on the determination.

The method of paragraph 20, further comprising determining whether, during treatment, one of the physiologic measurements does not reach the levels associated with previous treatments, and altering the energy delivery of a current treatment protocol and the future treatment protocol.

The method of paragraph 20, wherein the energy delivery is altered by changing the frequency, duration, or amplitude of the electrical pulse stimulation.

The method of paragraph 20, wherein the energy delivery is altered by changing the frequency or duration of the heating component.

The method of paragraph 20, wherein blood perfusion or electrical impedance measurements are compared to a predetermined value, and the therapeutic delivery is altered until the diseased state resembles the predetermined value.

The method of paragraph 20, wherein cross-correlation is used to correlate blood perfusion or electrical impedance measurements from a template normal state to an unknown diseased state. The cross-correlation function is maximized when two signals have similar phase and frequency content.

The method of paragraph 20, further comprising tracking the extent of wound healing based on feedback from sensor recordings.

The method of paragraph 20, wherein the user is prompted to change the position of the electrodes based on the electrical impedance or other sensor recordings.

The method of paragraph 20, further comprising determining whether, after treatment, one of the physiologic measurements has returned to a range of values associated with a pre-treatment baseline, and notifying the user.

The method of paragraph 20, wherein a subject uses an application to photograph the damaged tissue as treatment progresses.

The method of paragraph 20, wherein photographs are uploaded using the application.

A system comprising:
a processing device;
a non-transitory computer-readable medium communicatively coupled to the processing device, wherein the processing device is configured to perform operations comprising:
receiving a data set associated with patient indicators of wound healing and stimulation data storing the data set;
generating treatment parameters based on the stored data by determining a relationship between initial treatment parameters and plurality of the indicators of wound healing and the stimulation data;
electronically converting the stored data into the next parameters based on the relationship; and
generating an interface for display that includes data associated with the indicators of wound healing and the stimulation data.

We claim:

1. A therapeutic device for an ulcer on a limb of a patient, the limb having skin, the ulcer extending over an area of the limb, and said therapeutic device comprising:
a limb covering configured to cover the limb of the patient, the limb including the ulcer, said covering including a heating component adapted to cover the ulcer and beyond the area of the ulcer and to cover at least 40% of the limb and including a heat source that generates heat to apply and transfer the heat to the limb through the skin and to the ulcer and beyond the ulcer and to at least 40% of the limb to globally warm the limb and the ulcer to raise the temperature of the limb and not just provide local warming of the skin and the area of ulcer;
said covering adapted to off load pressure on the area of the ulcer wherein said covering does not apply pressure or shear on the ulcer;
a plurality of electrodes adapted to apply to the limb spaced from the area of ulcer;
an electrical pulse generator adapted to be in electrical communication with an electrical supply and electrically coupled with the plurality of electrodes, the electrical pulse generator being configured to generate a plurality of electrical impulses at least one of the electrodes when coupled with the electrical supply for delivering electrical pulse stimulation to the patient through the at least one of the electrodes wherein the electrical pulse generator is configured to apply a biphasic wave form in a range of 0.25 mA to 100 mA with a pulse width in a range of 50 to 500 microseconds;
and
a control unit in communication with a sensor and configured to control the pulse generator and the heating component to apply heat and electrical impulses at the same time to the limb.

2. The device according to claim 1, wherein the limb is a leg wherein the covering is sized and configured as a boot to cover the leg.

3. The device of claim 2, wherein the heating component has a footprint, the covering including a thermally conductive layer configured to transfer heat from the heat source to a greater area than a footprint of the heating component to increase the heat transfer efficiency of the heating component.

4. The device of claim 3, wherein the covering includes a plurality of layers, said plurality of layers including said thermally conductive layer and an inner layer for contacting the patient's skin, said thermally conductive layer being located between said heating component and said inner layer.

5. The device of claim 2, wherein the covering includes a plurality of layers, said plurality of layers including a thermally reflective layer and an inner layer for contacting the patient's skin, said heating component being located between the thermally reflective layer and the inner layer.

6. The device of claim 2, wherein the heating component is configured to cover at least at least 50% of the leg and apply heat to at least 50% of the leg.

7. The device of claim 1,
wherein the control unit is configured to adjust the electrical pulse generator and/or heating component based on input from said sensor.

8. The device of claim 7, wherein said sensor comprises a first sensor, further comprising a second sensor, said second sensor configured to detect, read and/or measure at least one other physiological characteristic of the patient that is indicative of wound healing, the at least one other physiological characteristic of the patient being selected from the group consisting of moisture, pH, and bioimpedance, and the control unit in communication with the first and second sensors to monitor wound healing based on signals from or states of the first and second sensors.

9. The device of claim 8, wherein the second sensor is configured to measure pH.

10. The device of claim 8, wherein the second sensor is configured to measure bioimpedance of the skin of the limb.

11. The device of claim 10, wherein the second sensor is further configured to measure the pH of the skin of the limb to detect an indication of infection and thereby measure at least one indicator of wound healing.

12. The device of claim 8, wherein the control unit is configured to adjust the electrical pulse generator to adjust the electrical impulses based on input from said second sensor.

13. The device according to claim 8, wherein the control unit is configured to control the heating component and/or the electrical pulse generator based on input from said first sensor and/or said second sensor.

14. The device of claim 8, wherein the control unit includes a communication device for transmitting information from said first and/or second sensor to a remote device.

15. The device of claim 1, wherein said sensor detects blood perfusion in the area of the ulcer.

16. The device of claim 1, wherein said control unit is in communication with said sensor.

17. A method of applying energy to a limb of a patient with a pressure ulcer, the limb having skin, said method comprising:
covering at least 40% of the limb of the patient containing the ulcer with the device of claim 10;
placing the electrodes on the limb based on input from the second sensor;
warming at least 40% of the limb by applying heat to at least 40% of the limb using the device;
said warming includes raising the temperature of the limb and not just local warming where just the skin of the limb and tissue beneath the skin of the limb are warmed; and
selectively applying electrical stimulation to the limb through the skin of the limb using the device.

18. A therapeutic device for an ulcer on a foot of a leg of a patient, the foot having skin, the ulcer extending over an area of the foot, and said therapeutic device comprising:
a foot covering configured as a boot to cover the foot and a portion of the leg of the patient, said covering including a heating component adapted to cover the area and beyond the area and to cover at least 40% of the leg and including a heat source that generates heat to apply and transfer the heat to the area and beyond the area and to at least 40% of the leg through the skin of the leg to globally warm the leg and the area of the ulcer to raise the temperature of the leg and not just provide local warming of the skin and the ulcer;
a plurality of electrodes adapted to apply to the leg spaced from the area of ulcer;
an electrical pulse generator adapted to be in electrical communication with an electrical supply and electrically coupled with the plurality of electrodes, the electrical pulse generator being configured to generate a plurality of electrical impulses at least one of the electrodes when coupled with the electrical supply for delivering electrical pulse stimulation to the patient through the at least one of the electrodes wherein the electrical pulse generator is configured to apply a biphasic wave form in a range of 0.25 mA to 100 mA with a pulse width in a range of 50 to 500 microseconds;
a first sensor, said first sensor configured to detect, read and/or measure bioimpedance;
a second sensor, said second sensor configured to detect, read and/or measure a physiological characteristic of the patient selected from the group consisting of moisture, blood flow, and pH; and
a control unit in communication with said first and second sensors and configured to power the pulse generator and the heating component and to apply heat and electrical impulses to the leg at the same time, and the control unit monitoring the biompedance based on input from said first sensor and monitoring wound healing based input from on said second sensor.

19. The device of claim 18, wherein the control unit is configured to control the electrical pulse generator and/or the heating component based input from at least said first sensor or said second sensor.

20. The device of claim 18, wherein the control unit includes a communication device for transmitting a signal from or a state of said first or second sensor to a remote device.

21. A therapeutic device for damaged tissue on a limb of a patient, the limb having skin, the damaged tissue extending over an area of the limb, and said therapeutic device comprising:
a covering configured to cover the limb of the patient, said covering including a heating component adapted to cover the area and beyond the area and to cover at least 40% of the limb and to apply heat to the area and beyond the area and to at least 40% of the limb to globally warm the limb and the area of the damaged tissue to raise the temperature of the limb and not just local warming of the skin and area of the damaged tissue;
said covering adapted to off load pressure on the area to avoid constricting the limb;
a plurality of electrodes adapted to apply to the limb;
an electrical pulse generator adapted to be in electrical communication with an electrical supply and electrically coupled with the plurality of electrodes, the electrical pulse generator being configured to generate a plurality of electrical impulses at at least one of the electrodes when coupled with the electrical supply for delivering electrical pulse stimulation to the patient through the at least one of the electrodes; and
a control unit configured to control the pulse generator and the heating component wherein the control unit is configured to adjust said covering to off load pressure on the area to avoid constricting the limb.

* * * * *